United States Patent
Nagumo et al.

(10) Patent No.: US 10,722,734 B2
(45) Date of Patent: Jul. 28, 2020

(54) X-RAY ENERGY DISTRIBUTION MEASUREMENT APPARATUS AND X-RAY THERAPY APPARATUS

(71) Applicant: Hitachi, Ltd., Tokyo (JP)

(72) Inventors: Yasushi Nagumo, Tokyo (JP); Takahiro Tadokoro, Tokyo (JP); Yuichiro Ueno, Tokyo (JP); Katsunori Ueno, Tokyo (JP); Kouichi Okada, Tokyo (JP); Shuichi Hatakeyama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/307,500

(22) PCT Filed: Jun. 28, 2016

(86) PCT No.: PCT/JP2016/069093
§ 371 (c)(1),
(2) Date: Dec. 6, 2018

(87) PCT Pub. No.: WO2018/003003
PCT Pub. Date: Jan. 4, 2018

(65) Prior Publication Data
US 2019/0175950 A1 Jun. 13, 2019

(51) Int. Cl.
*A61N 5/10* (2006.01)
*G01T 1/20* (2006.01)
*G01T 1/202* (2006.01)

(52) U.S. Cl.
CPC .............. *A61N 5/1071* (2013.01); *G01T 1/20* (2013.01); *G01T 1/2023* (2013.01);
(Continued)

(58) Field of Classification Search
None
See application file for complete search history.

(56) References Cited

U.S. PATENT DOCUMENTS

| 5,856,673 A | 1/1999 | Ikegami et al. |
| 2003/0095625 A1 | 5/2003 | Steinberg |

(Continued)

FOREIGN PATENT DOCUMENTS

| JP | 04-132987 A | 5/1992 |
| JP | 09-230053 A | 9/1997 |

(Continued)

OTHER PUBLICATIONS

Katsunori Ueno, et al., "Development of a optical fiber type dosimeter using near infrared luminescence", Japanese Journal of Medical Physics, Sep. 2015, vol. 35 Supplement No. 3, p. 77.

(Continued)

*Primary Examiner* — Hoon K Song
(74) *Attorney, Agent, or Firm* — Mattingly & Malur, PC

(57) ABSTRACT

The radiation detection device includes a plurality of radiation detectors arranged in a row and is inserted into the body of patient subjected to the X-ray therapy. An X-ray detection signal (photon) is output from each of the radiation detectors that detects the X-ray applied to the patient. The dose rate measurement device separately connected to each of the radiation detectors obtains the dos rate at the position of each radiation detector based on the signals. The irradiation direction determination device determines whether the row of radiation detectors matches the irradiation direction of the X-ray using the dos rate obtained by each of the dose rate measurement devices. When the row of radiation detectors matches the irradiation direction, the energy distribution analysis device obtains an energy distribution using the dose rate at the positions of the radiation detectors by applying, for example, an inverse problem analysis called an unfolding method.

10 Claims, 11 Drawing Sheets

(52) U.S. Cl.
CPC .......... *A61N 5/1067* (2013.01); *A61N 5/1081* (2013.01); *A61N 2005/1091* (2013.01)

(56) References Cited

U.S. PATENT DOCUMENTS

| | | |
|---|---|---|
| 2009/0209812 A1 | 8/2009 | Omoto |
| 2014/0221724 A1* | 8/2014 | Beddar ................ A61N 5/1048 600/1 |
| 2015/0301202 A1 | 10/2015 | Takagi et al. |
| 2017/0368373 A1* | 12/2017 | Sahadevan ........... A61N 5/1084 |
| 2018/0085597 A1* | 3/2018 | Isham .................. A61N 5/1014 |

FOREIGN PATENT DOCUMENTS

| | | |
|---|---|---|
| JP | 11-160437 A | 6/1999 |
| JP | 2001-056381 A | 2/2001 |
| JP | 2003-098259 A | 4/2003 |
| JP | 2003-210596 A | 7/2003 |
| JP | 2007-114067 A | 5/2007 |
| JP | 2009-189653 A | 8/2009 |
| JP | 2013-183756 A | 9/2013 |
| JP | 2015-204985 A | 11/2015 |

OTHER PUBLICATIONS

Takahiro Tadokoro, et al., "Current status and vision of study for severe accident instrumentation system, 1. Optical fiber-type radiation monitor system", 2015 Annual Meeting of the Atomic Energy Society of Japan Proceedings, Lecture No. 117, issued on Mar. 5, 2015.
International Search Report of PCT/JP2016/069093 dated Oct. 4, 2016.

* cited by examiner

X-RAY ENERGY DISTRIBUTION MEASUREMENT APPARATUS AND X-RAY THERAPY APPARATUS

TECHNICAL FIELD

The present invention relates to an X-ray energy distribution measurement apparatus and an X-ray therapy apparatus, and particularly to an X-ray energy distribution measurement apparatus and an X-ray therapy apparatus suitable to measure an X-ray energy distribution in the body during X-ray therapy.

BACKGROUND ART

In Japan, the first cause of death is cancer, and cancer is steadily increasing. In recent Japan in which improvement in quality of life (QOL) is needed, therapy using radiation attracts attention as a cancer therapy method. In order to improve the QOL as the need, a radiation cancer therapy technique which is a seed becomes highly accurate, and radiation cancer therapy also starts to be widespread in Japan.

Radiation used for therapy includes an X-ray, a particle beam (a proton beam or a heavy particle beam), an electron beam, and a neutron beam. Particularly, in recent years, a particle beam therapy apparatus using a proton beam and a heavy particle beam therapy apparatus using a heavy particle beam (for example, a carbon beam) have been remarkably developed. A patient is irradiated with a particle beam by using the property that the proton beam and the heavy particle beam generate a dose peak (black peak) by being intensively applied with energy immediately after being stopped, and thus a dose can be applied to an affected part of cancer in a concentration manner, so that low invasive and highly accurate cancer therapy can be expected.

Also in cancer therapy using an X-ray, intensity-modulated radiotherapy (IMRT) and image-guided radiotherapy (IGRT) have been developed, and an effort to cause a dose in X-ray irradiation to concentrate on an affected part of cancer has been made. In accordance with sophistication of a radiation therapy apparatus, there is the need for improvement of the whole accuracy related to radiation therapy, such as the accuracy of a therapy plan and the accuracy of patient positioning, dose rate measurement for quality assurance (QA) of a therapy plan and a therapy apparatus.

In radiation therapy, a total amount of damage received by an affected part is evaluated on the basis of a total amount of (absorbed dose) energy applied to the affected part of cancer due to radiation, and a therapy plan for a patient is made on the basis of the evaluation. In the radiation therapy, a dose rate is measured in order to obtain the absorbed dose. In the radiation therapy, an ionization chamber of which stability and reproducibility are favorable are widely used to measure a dose rate of radiation applied to a patient. However, the ionization chamber has a limit in miniaturization due to a detection principle thereof, and, instead thereof, a dose distribution measurement using a semiconductor detector which is relatively easily miniaturized is performed. In a case where even a signal processing system is included, the semiconductor detector also has a limit in miniaturization. Since a high voltage is required to be applied in such a radiation detector, it is difficult to insert the radiation detector into a patient's body, and to measure a dose rate. Such a detector generally has high density, has a greater interaction with radiation than a substance in the body and water, and thus the influence of the radiation detector cannot be disregarded.

As described above, in a situation in which an actual internal absorbed dose cannot be understood, a dose distribution of an affected part obtained through therapy planning has a margin by taking into consideration body motion of the patient due to respiration or the like. This is a cause of reducing the irradiation accuracy of radiation to an affected part. In the body of a patient, in a case where a normal part sensitive to radiation is present near an affected part which is a therapy target part, radiation therapy of the affected part is difficult.

Therefore, a method of predicting an internal absorbed dose by using a radiation detector disposed outside the body of a patient is effective, and there are the following prediction techniques.

A radiation therapy apparatus disclosed in JP-A-2003-210596 is an electron beam therapy apparatus, and irradiates an affected part of a patient with an electron beam. An electron gun and a linear accelerator are provided in a rotated gantry, and an electron beam generated from the electron gun is accelerated in the linear accelerator, and is then applied to an affected part of a patient on a bed from an irradiation head. The electron beam applied to the affected part and transmitted through the patient is detected by a radiation detector which is disposed at a lower part of the bed directly under the affected part. A dose applied to the affected part is obtained on the basis of a radiation detection signal output from the radiation detector.

In the radiation therapy apparatus disclosed in JP-A-2003-210596 (US2003/0095625A1), radiation transmitted through the patient is detected by a radiation detector disposed outside the body of the patient irradiated with the radiation, and thus there is a possibility that an accurate internal absorbed dose cannot be measured. Temporal changes of a position of an organ (affected part) in the body and a size of the organ in a radiation irradiation direction between the time of therapy planning and the time of therapy execution on the affected part using irradiation with radiation, and patient positioning during therapy also cause errors. An internal dose distribution of the patient is estimated through calculation using a dose which is obtained on the basis of a radiation detection signal output from the radiation detector outside the body. A calculation error in this estimation cannot be disregarded.

In order to reduce such errors, a radiation detector is preferably inserted into the body. A radiation detector inserted into the body is disclosed in JP-A-2001-56381. The radiation detector has a scintillation fiber, and an optical fiber is connected to the scintillation fiber via a band-pass filter. JP-A-2001-56381 discloses a technique in which the scintillation fiber and the optical transmission fiber are inserted into the body, and thus contribution of Cherenkov light which is noise can be removed such that a true radiation dose can be measured.

"Bragg Curve Measurement in Near-Infrared Single Photon Counting Mode", Katsunori UENO and others, the 110th Japanese Society of Health and Medical Sociology, Vol. 35, Supplement No. 3 (September, 2015), page 77 discloses an optical fiber type online dosimeter (internal dosimeter) which can measure an irradiation dose applied to a patient during proton therapy. The optical fiber type online dosimeter uses Nd:YAG for a detection unit, and performs single-photon counting on near-infrared light generated by Nd:YAG.

"Current status and vision of study for severe accident instrumentation system, 1. Optical fiber-type radiation monitor system", Takahiro TADOKORO and others, 2015 Annual Meeting of the Atomic Energy Society of Japan Proceedings, Lecture No. 117, issued on Mar. 5, 2015, discloses an optical fiber type radiation monitor, applied to a nuclear power plant, is configured with a detection unit, an optical fiber unit, and an optical measurement unit using Nd:YAG. The optical fiber type radiation monitor can measure a dose rate with the accuracy equal to or lower than ±4% FS in a range of a dose rate of $1.0 \times 10^{-2}$ to $9.54 \times 10^{4}$ Gy/h.

In an X-ray therapy apparatus, an energy spectrum of an X-ray has a very wide distribution according to an X-ray generation principle that an accelerated electron collides with a target such as tungsten, and an X-ray is generated due to braking radiation occurring at that time. JP-A-2015-204985 (US2015/0301202A1) discloses an X-ray energy spectrum measurement method which is an example of a method of measuring an energy spectrum. In the X-ray energy spectrum measurement method, X-rays are applied to respective portions of which thicknesses are different from each other by using an attenuation member of which a thickness changes stepwise, and energy of each X-ray transmitted through each portion is obtained by using the Bayesian inference formula. Energy of a signal output from a radiation detector which detects an X-ray transmitted through a subject is corrected by using the obtained energy of an X-ray.

In a radiation detection system disclosed in JP-A-2007-114067, a scintillator layer is formed on an inner surface of each of two optical fibers which are disposed in parallel and to which X-rays are incident, and an X-ray transmitted through one optical fiber is incident to the other optical fiber. Information regarding a radiation flying direction is generated on the basis of a signal output from the scintillator layer of each optical fiber. The information regarding a flying direction is created on the basis of, for example, a calculated incidence time point, the incidence time point at which radiation is incident to each optical fiber being calculated on the basis of an output signal from each scintillator layer.

JP-A-11-160437 discloses an optical fiber type radiation detector. In the optical fiber type radiation detector, a plurality of (for example, seven) optical fibers are inserted into a scintillator. Light generated in the scintillator when radiation is incident to the scintillator is transmitted to a counter through the optical fibers, and the number of pulses is counted by a counter.

An endoscope system disclosed in JP-A-2009-189653 (US2009/0209812A1) includes a rotary self-propelled endoscope, a first control device, a second control device, and an aspirator. The rotary self-propelled endoscope has an insertion section and an operation section. The insertion section has in an order from the distal end thereof: an insertion section main body having a distal end portion and a bending portion; an insertion assistance device; an insertion section receiving case; a distal end side guide tube which is a corrugated tube interposed between the insertion assistance device and the insertion section receiving case; an external drive section (second drive section) which is provided on an outer surface of the distal end side guide tube; a coupling section which is provided in the insertion section receiving case; and an operation section side guide tube which is a corrugated tube interposed between the operation section and the coupling section. The operation section has a motor unit (first drive section), a grasping section, and a main operation section which is an operation instruction section.

The insertion section main body configuring the insertion section has an outer shaft and an inner shaft rotatably inserted into the outer shaft. The outer shaft (driving force generation portion) is provided with a coil which is wound not densely and is biocompatible, and a resin thin film, which links between the striae of the coil, is biocompatible and covers the coil. The inner shaft is rotatably inserted into the outer shaft, and is configured to allow the distal end portion of the insertion section main body to rotate with good following capability by reducing torsion of the insertion section main body. In order to obtain anti-torsion property, the inner shaft includes a first coil which is wound not densely in the normal direction and is biocompatible, a second coil which is wound not densely in the direction opposite to that of the first coil to be disposed between the striae of the first coil and which is biocompatible, a third coil which is wound not densely in the opposite direction (normal direction) to that of the second coil, to be disposed between the striae and on the outer periphery of the second coil and which is biocompatible, and a resin thin film which links between the striae of the third coil, covers the third coil, and is biocompatible.

Each distal end of the outer shaft and the inner shaft is fixed to a distal end supporting section which is rotatably connected to the insertion section main body including the distal end portion and bending portion, via adhesive joints. An imaging unit is provided at the distal end portion, and a cable tube having a cable built thereinto which is connected to the imaging unit is provided inside the inner shaft.

The first control device is connected to a footswitch, via a cable, which enables an operation to start or stop the rotations of the outer shaft which is a rotary cylindrical body and the inner shaft which is a torque transmission member. The second control device is connected to the aspirator.

The outer shaft is rotated by an external drive section. The external drive section includes a first roller, a second roller, a third roller, and a first motor connected to the first roller. The first roller, the second roller, and the third roller are disposed to be inclined such that the circumferential direction of each periphery surface is generally along the direction of the helical configuration formed on the surface of the outer shaft. The first roller is rotated due to driving of the first motor, and thus the outer shaft is rotated. The inner shaft is rotated due to driving a second motor included in the motor unit. When a rotation control command is output from the first control device by operating the footswitch, the first motor and the second motor are rotated, and when a stop control command is output from the first control device, the first motor and the second motor are stopped. JP-A-2009-189653 is referred to with respect to detailed configurations and operations of the endoscope system.

CITATION LIST

Patent Literature

PTL 1: JP-A-2003-210596
PTL 2: JP-A-2001-56381
PTL 3: JP-A-2015-204985
PTL 4: JP-A-2007-114067
PTL 5: JP-A-11-160437
PTL 6: JP-A-2009-189653

Non-Patent Literature

NPL 1: "Bragg Curve Measurement in Near-Infrared Single Photon Counting Mode", Katsunori UENO and others, the 110th Japanese Society of Health and Medical Sociology, Vol. 35, Supplement No. 3 (September, 2015), page 77

NPL 2: "Current status and vision of study for severe accident instrumentation system, 1. Optical fiber-type radiation monitor system", Takahiro TADOKORO and others, 2015 Annual Meeting of the Atomic Energy Society of Japan Proceedings, Lecture No. 117, issued on Mar. 5, 2015

SUMMARY OF INVENTION

Technical Problem

By using the radiation detector disclosed in JP-A-2001-56381, or "Bragg Curve Measurement in Near-Infrared Single Photon Counting Mode", Katsunori UENO and others, the 110th Japanese Society of Health and Medical Sociology, Vol. 35, Supplement No. 3 (September, 2015), page 77, the radiation detector can be inserted into the body of a patient, and thus a dose rate of radiation applied to an affected part can be measured with high accuracy. An energy distribution of an X-ray detected by the radiation detector may be obtained according to the X-ray energy spectrum measurement method disclosed in JP-A-2015-204985.

In a case where radiation is detected by radiation detectors, the radiation detectors are required to be disposed such that detection surfaces thereof face each other in a radiation irradiation direction. However, it is hard to detect directions in which the detection surfaces of the radiation detectors inserted into the body are directed, and it is also hard to dispose the radiation detectors such that detection surfaces thereof face each other in a radiation irradiation direction.

An object of the present invention to provide a radiation energy distribution monitoring apparatus and an X-ray therapy apparatus capable of obtaining an X-ray energy distribution in the body with high accuracy.

Solution to Problem

According to an aspect of the present invention for achieving the object, there is provided an X-ray energy distribution measurement apparatus including:

a radiation detection device that has a plurality of radiation detectors each including a light emitting portion to which an X-ray is incident and arranged linearly in a line, and is insertable into the body;

a dose rate measurement device that is connected to an optical fiber connected to the light emitting portion, receives a photon output from the light emitting portion, and obtains a dose rate at a position of the radiation detector on the basis of the photon;

an irradiation direction determination device to which the dose rate is input from each dose rate measurement device separately connected to the light emitting portion of each of the radiation detectors, and determines whether or not a string of the radiation detectors including the plurality of radiation detectors arranged in a line, included in the radiation detection device, matches an X-ray irradiation direction on the basis of the input dose rate; and an energy distribution analysis device that obtains an X-ray energy distribution on the basis of the dose rate at each position of the plurality of radiation detectors included in the string of the radiation detectors matching the irradiation direction in a case where the irradiation direction determination device determines that the string of the radiation detectors matches the X-ray irradiation direction.

Even in a case where the radiation detection device is inserted into the body, it is possible to determine whether or not a string of radiation detectors including a plurality of radiation detectors arranged in a line matches an X-ray irradiation direction, by using a dose rate at a position of each of the radiation detector arranged in a line, obtained by the dose rate measurement device on the basis of photon output from each of the plurality of radiation detectors arranged linearly in a line. In a state in which the string of radiation detectors of the radiation detection device matches the X-ray irradiation direction, an X-ray applied to an affected part of a patient is detected by each radiation detector included in the string of radiation detectors, a dose rate at a position of each radiation detector inserted into the body, included in the string of radiation detectors, is obtained on the basis of the photon from the radiation detector, and energy in the affected part is obtained by using the dose rate. Therefore, it is possible to obtain an energy distribution in the vicinity of the affected part irradiated with an X-ray with high accuracy.

Advantageous Effects of Invention

According to the present invention, it is possible to obtain an X-ray energy distribution in the body irradiated with an X-ray with high accuracy.

DESCRIPTION OF EMBODIMENTS

Figure 1:
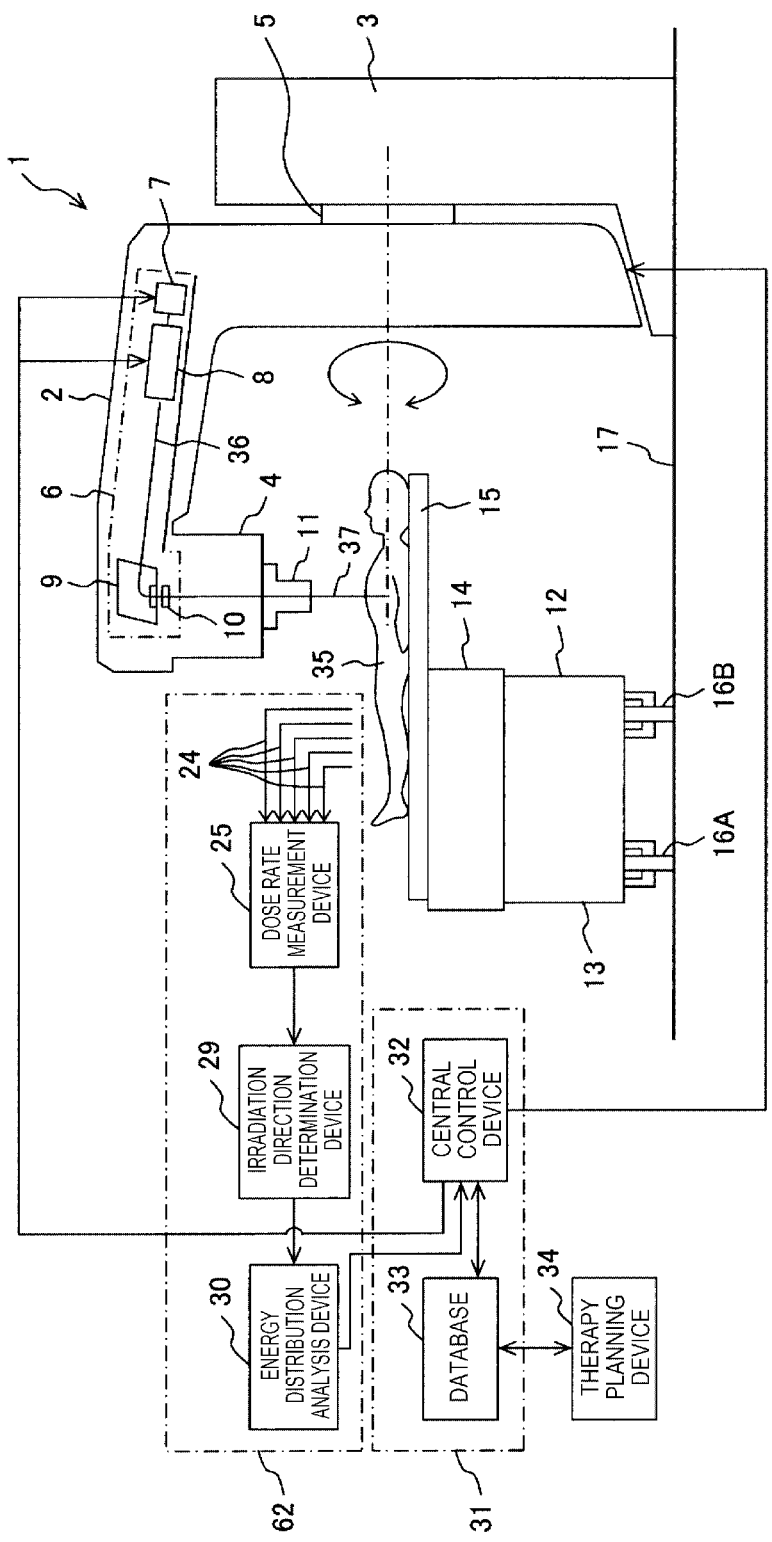
FIG. 1 is a configuration diagram of an X-ray therapy apparatus of Example 1 which is one preferable example of the present invention.

Examples of the present invention will be described below.

Example 1

A description will be made of an X-ray therapy apparatus of Example 1 which is one preferable example of the present invention with reference to FIG. 1.

An X-ray therapy apparatus 1 of the present example includes a rotation gantry 2, a trestle 3, an irradiation head 4, an X-ray generation device 6, a variable collimator 11, a therapy table 12, a control system 90, and an X-ray energy distribution measurement apparatus 62. The X-ray therapy apparatus 1 is provided on a floor in a treatment room (not illustrated).

A rotation shaft 5 provided at the rotation gantry 2 is rotatably attached to the trestle 3 provided on the floor of the treatment room, so as to be supported by the trestle 3. A motor (not illustrated) is installed in the trestle 3, and rotation of the motor is decelerated by a deceleration mechanism (not illustrated) installed in the trestle 3 so as to be delivered to the rotation shaft 5. The irradiation head 4 is provided at a distal end of an arm portion of the rotation gantry 2 so as to face a bed 15 which will be described later. The variable collimator 11 is attached to a front end of the irradiation head 4, and faces the bed 15. The X-ray generation device 6 is provided in the arm portion. The X-ray generation device 6 includes an electron beam generation portion (for example, an electron gun) 7, a linear accelerator 8, a deflection electromagnet 9, and a target 10. The electron beam generation portion 7 is connected to the linear accelerator 8. The deflection electromagnet 9 is disposed near the irradiation head 4 at the distal end of the arm portion. The target 10 faces the deflection electromagnet 9, and is disposed further toward the irradiation head 4 side than the deflection electromagnet 9.

The therapy table 12 is installed on the floor of the treatment room, and includes drive mechanisms 12 and the bed 15. The drive mechanisms 12 include an X direction drive mechanism 13, a vertical direction drive mechanism 14, and a Y direction drive mechanism (not illustrated). The X direction drive mechanism 13 is installed so as to be movable along guide rails 16A and 16B installed on the floor of the treatment room. The vertical direction drive mechanism 14 is installed on the X direction drive mechanism 13, and the Y direction drive mechanism is provided on the vertical direction drive mechanism 14. The bed 15 is installed on the Y direction drive mechanism. The Y direction drive mechanism moves the bed 15 in an axial direction of the rotation shaft 5. The X direction drive mechanism 13 moves the bed 15 in a direction orthogonal to a movement direction of the Y direction drive mechanism. The vertical direction drive mechanism 14 moves the bed 15 in a vertical direction.

Figure 2:
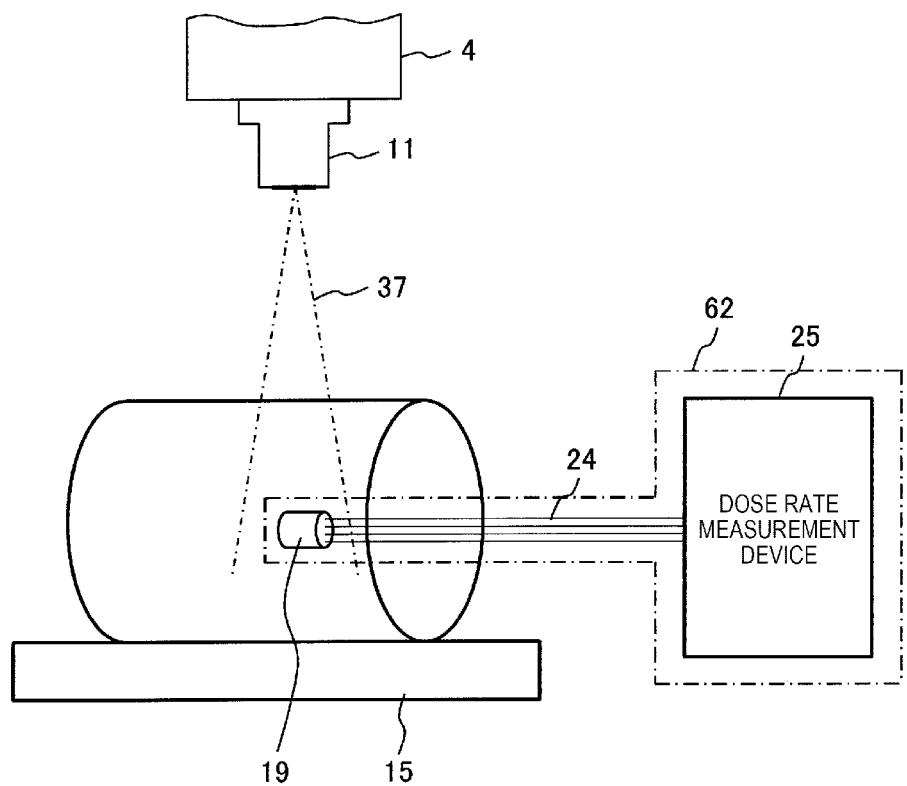
FIG. 2 is a schematic diagram illustrating a radiation detection device inserted into the body of a patient on a bed illustrated in FIG. 1.

The X-ray energy distribution measurement apparatus 62 includes, as illustrated in FIGS. 1 and 2, a radiation detection device 19, a dose rate measurement device 25, an irradiation direction determination device 29, and an energy distribution analysis device 30. The radiation detection device 19 has a configuration in which a plurality of (for example, seven) radiation detectors 21 arranged in a line are attached to a support member 20 (refer to FIGS. 3 and 4). A gap between the respective radiation detectors 21 arranged in a line is preferably an equal gap, but may be an unequal gap as long as such a gap can be accurately understood.

Figure 5:
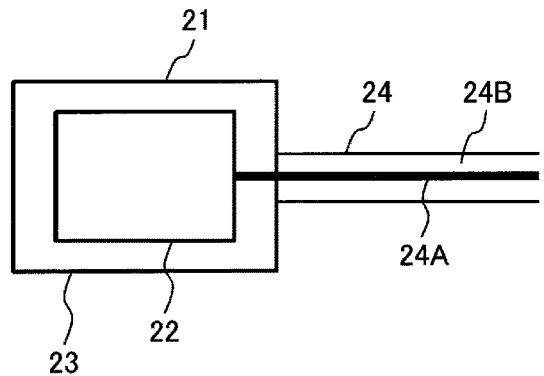
FIG. 5 is a detailed configuration diagram of one radiation detector included in the radiation detection device illustrated in FIG. 3.

As illustrated in FIG. 5, the radiation detector 21 has a cover 23 and a light emitting portion 22. The entire surface of the light emitting portion 22 is covered with the cover 23. The light emitting portion 22 is made of a radiation light emitting material which generates light with the intensity depending on an amount of incident radiation (for example, an X-ray). The radiation light emitting material contains, for example, at least one species of rare earth elements such as ytterbium, neodymium, cerium, and praseodymium in a base material such as transparent yttrium aluminum garnet (YAG). As mentioned above, since the radiation light emitting material contains at least one rare earth element, it is possible to improve linearity between a dose rate of radiation incident to the light emitting portion 22 and the intensity of light emitted from the light emitting portion 22 due to the incident radiation. Thus, the radiation detector 21 can more accurately measure a dose rate of radiation even if radiation with a high dose rate is incident. In the present example, the light emitting portion 22 is made of, for example, Nd:YAG (YAG containing neodymium).

Instead of Nd:YAG, the light emitting portion 19 may employ any of NdCe:YAG, Yb:YAG, Yb:LuAG, Nd:YVO$_4$, Tm:YVO$_4$, Tm:YAG, Yb:YVO$_4$, Eu:YVO$_4$, Nd:GdVO$_4$, Ce:LiSAF, Ce:LiCAF, Ce:LiSGaF, Nd:YLF, Pr:YLF, Er:YLF, Ho:YLF, Yb:KGW, and Nd:KGW. Each of such all materials contains at least one rare earth element. As a radiation light emitting material, in addition to YAG, there are LuAG, YVO$_4$, GdVO$_4$, and YLF as described above.

The cover 23 transmits radiation (for example, an X-ray) therethrough, but is made of a material having light blocking property of blocking external light from being incident to the light emitting portion 22. A material used in the cover 23 is, for example, aluminum. The cover 23 made of a light blocking material reflects the light generated by the light emitting portion 22 toward the light emitting portion 22. When it is taken into consideration that the radiation detector 21 is inserted into the body, an outer surface of the cover 23 brought into contact with an internal organ is required to be made of a stable and harmless material.

In the light emitting portion 22 made of Nd:YAG, hereinafter, a description will be made of a process in which a photon p is generated when radiation is incident. In a case where an X-ray is incident to the light emitting portion 22, a rare earth atom in the light emitting portion 22 is caused to transition to an excitation state (higher energy level). On the other hand, when the rare earth atom having high energy present in the higher energy level transitions to an excitation state in which energy is lower, the photon p having energy corresponding to difference in the energy is generated.

As illustrated in FIG. 5, an optical fiber 24 has a core 24A located at the center, and a clad 24B surrounding the core 24A. In a case where the optical fiber 24 is actually used, an outer surface of the clad 24B is coated with, for example, PVC. The core 24A is connected to the light emitting portion 22. The core 24A is made of, for example, quartz or plastic. The light emitting portion 22 of each radiation detector 21 of the radiation detection device 19 is separately connected to the optical fiber 24.

An outer diameter of each of the radiation detector 21 and the optical fiber 24 is about 1 mm. A width of the radiation detection device 19 in a direction in which the plurality of radiation detectors 21 of the radiation detection device 19 are arranged, that is, a width of the support member 20 is less than 1 cm.

Figure 6:
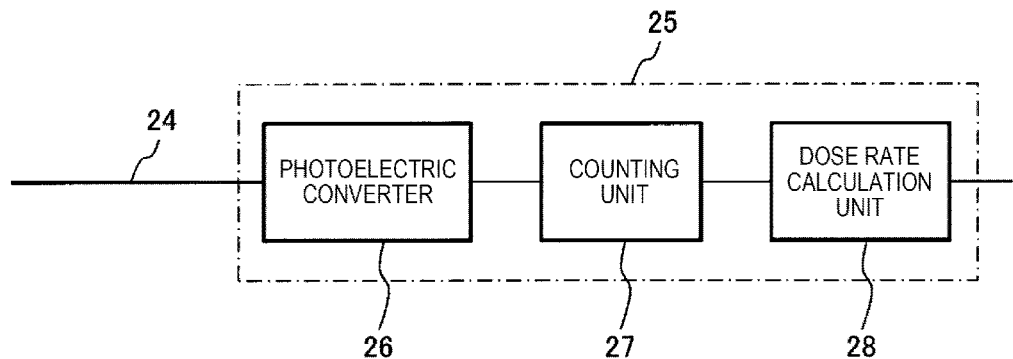
FIG. 6 is a detailed configuration diagram of a dose rate measurement device illustrated in FIG. 1.

The optical fiber 24 is connected to the dose rate measurement device 25 (refer to FIGS. 1 and 2). As illustrated in FIG. 6, the dose rate measurement device 25 includes a photoelectric converter 26, a counting unit 27, and a dose rate calculation unit 28. The optical fiber 24 is connected to the photoelectric converter 26. As the photoelectric converter 26, a photomultiplier tube or a photodiode (for example, an avalanche photodiode) is used. The photoelectric converter 26 is a converter which transmits a single electric pulse for each photon p which is input through the optical fiber 24. Light (photon) can be converted into an electric pulse of which a current is amplified by using the photoelectric converter 26. The counting unit 27 is connected to the photoelectric converter 26, and the dose rate calculation unit 28 is connected to the counting unit 27. The counting unit 27 is connected to the photoelectric converter 26 via an amplifier (not illustrated) which amplifies an electric pulse. The counting unit 27 counts input electric pulses, so as to obtain a counting rate of the electric pulses. The dose rate measurement device 25, specifically, the photoelectric converter 26, the counting unit 27, and the dose rate calculation unit 28 are provided for each radiation detector 21. The optical fiber 24 connected to each radiation detector 21 is separately connected to the photoelectric converter 26 of the dose rate measurement device 25.

Figure 8:
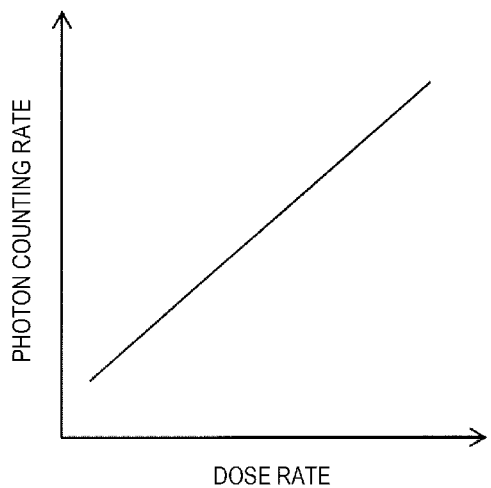
FIG. 8 is a characteristic diagram illustrating a relationship between a dose rate and a photon counting rate.

The dose rate calculation unit 28 stores, in a memory (not illustrated), a data table in which a dose rate of radiation and the number of photons (hereinafter, referred to as a photon counting rate) per unit time emitted in the light emitting portion 22, illustrated in FIG. 8, are correlated with each other. The data table substantially correlates a dose rate of radiation with an electric pulse output from the photoelectric converter 26. As illustrated in FIG. 8, a dose rate of an X-ray and a photon counting rate have a proportional relationship. The inventors have found that a dose rate of radiation incident to the light emitting portion 22 of the radiation detector 21 and a counting rate of photons (light) emitted in the light emitting portion 22 have a proportional relationship in a wide range, through tests. The proportional relationship between a dose rate of radiation and a photon counting rate is also established for the radiation detector 21 having the light emitting portion 22 made of the above-described materials other than Nd:YAG, containing rare earth elements other than Nd:YAG.

It is well known that there is a correspondence relationship on a one-to-one basis between a photon counting rate and a counting rate of electric pulses, and thus a counting rate of electric pulses output from the counting unit 27 can be converted into a dose rate of an X-ray incident to the radiation detector 21 by using the characteristics illustrated in FIG. 8. The correspondence relationship between a dose rate of an X-ray and a photon counting rate differs depending on a size, a shape, and a material of the light emitting portion 22 used in the radiation detector 21, and a thickness and a length of the optical fiber 24, and thus a correspondence relationship between a dose rate of an X-ray and a photon counting rate may be created as a data table according to the light emitting portion 22 and the optical fiber 24 to be used. Consequently, even in a case where sizes, shapes, and materials of the light emitting portion 22 and thicknesses and lengths of the optical fiber 24 are different from each other, a counting rate of electric pulses obtained in the counting unit 27 can be converted into a dose rate of an X-ray.

The dose rate calculation unit 28 of each dose rate measurement device 25 is connected to a single irradiation direction determination device 29, and the irradiation direction determination device 29 is connected to the energy distribution analysis device 30. A control system 31 includes a central control device 32 and a database 33. The database 33 is connected to the central control device 32 and a therapy planning device 34. The energy distribution analysis device 30 is connected to the central control device 32.

Figure 7:
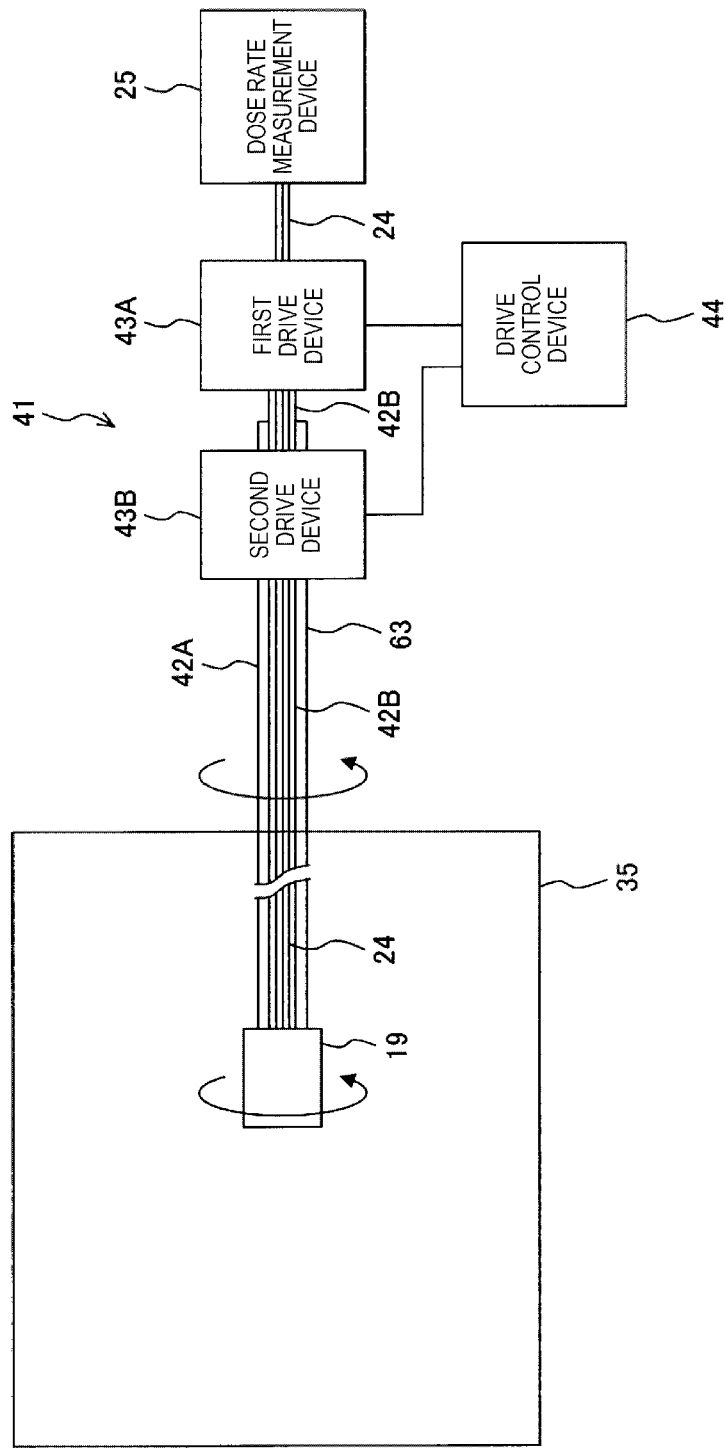
FIG. 7 is a configuration diagram of a sensor insertion device for inserting the radiation detection device illustrated in FIG. 3 into the body.

With reference to FIG. 7, a description will be made of a sensor insertion system 41 for inserting the radiation detection device 19 into the body of a patient 35. The X-ray energy distribution measurement apparatus 62 has the sensor insertion system 41. The sensor insertion system 41 has the same configuration as that of the rotary self-propelled endoscope disclosed in, for example, JP-A-2009-189653 (refer to FIG. 1 in JP-A-2009-189653). FIG. 7 schematically illustrating a configuration illustrated in FIG. 2 in JP-A-2009-189653. Although not illustrated, the sensor insertion system 41 includes a sensor insertion device (corresponding to the rotary self-propelled end disclosed in JP-A-2009-189653) 63 having an insertion section and an operation section, a first control device (corresponding to the first control device disclosed in JP-A-2009-189653) 44, a second control device (not illustrated), and an aspirator (not illustrated). As disclosed in JP-A-2009-189653, the insertion section has in an order from the distal end thereof: an insertion section main body having a distal end portion and a bending portion attached with the distal end portion; an insertion assistance device; an insertion section receiving case; a distal end side guide tube which is a corrugated tube interposed between the insertion assistance device and the insertion section receiving case; a second drive device (corresponding to an external drive section disclosed in JP-A-2009-189653) 43B which is provided on an outer surface of the distal end side guide tube; a coupling section which is provided on the operation section side of the insertion section receiving case; and an operation section side guide tube which is a corrugated tube interposed between the operation section and the coupling section. As disclosed in JP-A-2009-189653, the operation section has a first drive device (corresponding to the motor unit disclosed in JP-A-2009-189653) 43A, a grasping section, and a main operation section which is an operation instruction section.

The insertion section main body configuring the insertion section has an outer shaft 42A and an inner shaft 42B rotatably inserted into the outer shaft 42A (refer to FIG. 7). Although not illustrated, the outer shaft 42A and the inner shaft 42B are inserted into each of the insertion assistance device, the distal end side guide tube, the insertion section receiving case, and the coupling section which is provided in the insertion section receiving case, as disclosed in JP-A-2009-189653. The inner shaft 42B is inserted into the operation section side guide tube as disclosed in JP-A-2009-189653.

Figure 3:
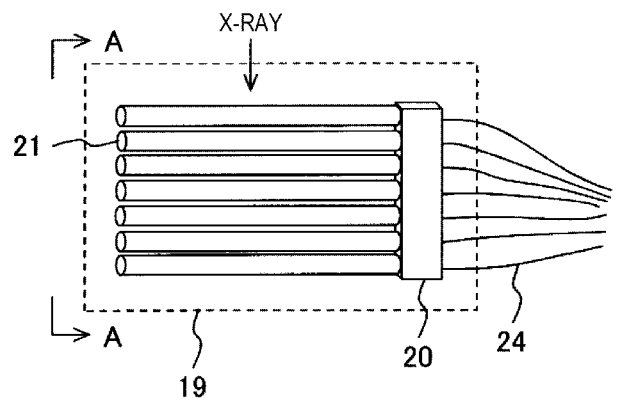
FIG. 3 is an enlarged view of the radiation detection device illustrated in FIG. 2.

The outer shaft (driving force generation portion) 42A of the sensor insertion device 63 is provided with a coil which is wound not densely and is biocompatible, and a resin thin film, which links between the striae of the coil, is biocompatible and covers the coil (refer to FIG. 3 in JP-A-2009-189653). The inner shaft 42B is rotatably inserted into the outer shaft 42A, and is configured to allow the distal end portion of the insertion section main body to rotate with good following capability by reducing torsion of the insertion section main body (refer to FIG. 4 in JP-A-2009-189653).

The first drive device 43A has configurations illustrated in FIGS. 2, 6, and 7 in JP-A-2009-189653, and rotates the inner shaft 42B by using a motor. The second drive device 43B has configurations illustrated in FIGS. 2 and 3 in JP-A-2009-189653, and rotates the outer shaft 42A by using another motor.

The support member 20 is attached to the tip of the distal end portion of the insertion section of the sensor insertion device 63, and thus the radiation detection device 19 is fixed to the sensor insertion device 63. The optical fiber 24 connected to each radiation detector 21 of the radiation detection device 19 is disposed in the inner shaft 42B, reaches the first drive device 43A, and is extracted from the first drive device 43A to the outside so as to be connected to the dose rate measurement device 25. The sensor insertion device 63 is an insertion device inserting the radiation detection device 19 into the body and is also a rotation device rotating the radiation detection device 19.

A description will be made of cancer therapy of a patient using the X-ray therapy apparatus 1. The patient 35 subjected to the X-ray therapy is placed on the bed 15 of the therapy table 12 (refer to FIGS. 1 and 2). As schematically illustrated in FIG. 2, a plurality of radiation detectors 35 are inserted into the body of the patient 35 on the bed 15. The radiation detection device 19 attached to the sensor insertion device 63 of the sensor insertion system 41 is inserted up to a position near an affected part by being inserted into any of the esophagus, the stomach, and the duodenum through, for example, the mouth or the nostrils, or into the large intestine through the anus, by operating the sensor insertion device 63 in the same manner as in the rotary self-propelled endoscope disclosed in JP-A-2009-189653. As the number of radiation detectors 21 included in the radiation detection device 19 inserted into the body is increased, a radiation energy distribution in the vicinity of an affected part irradiated with an X-ray can be measured with higher accuracy. Hereinafter, in a case where the number of radiation detectors 21 is increased, it is hard to insert the radiation detectors 21 into the body. Therefore, the number of radiation detectors 21 of the radiation detection device 19 may be determined by taking into consideration a size of an X-ray irradiation region in the body, position accuracy required to dispose the radiation detectors 21 in the body, and invasiveness of when the radiation detectors 21 are inserted into the body.

The bed 15 is moved by driving the drive mechanisms 12, and thus the affected part of the patient 35 is positioned at a central line of the irradiation head 4. In other words, the X direction drive mechanism 13 is moved along the guide rails 16A and 16B, and thus the affected part of the patient 35 on the bed 15 is aligned with the axial center of the rotation shaft 5 in the X direction. The vertical direction drive mechanism 14 is driven, and thus the affected part of the patient 35 on the bed 15 is aligned with the axial center of the rotation shaft 5 in the vertical direction. The Y direction drive mechanism is driven such that the bed 15 is moved in the axial direction of the rotation shaft 5, and thus the affected part is aligned with the central line of the irradiation head 4.

Before the patient 35 is placed on the bed 15, therapy planning for the affected part of the patient 35 is performed. In this therapy planning, therapy plan information such as an X-ray irradiation direction, a shape of the affected part viewed from the irradiation direction, a set dose for the affected part, and intensity and energy of an X-ray is created by using the therapy planning device 34. The created therapy plan information is input to the database 33 from the therapy planning device 34, and is stored in the database 33.

The central control device 32 reads the therapy plan information of the patient receiving the therapy from the database 33, and stores the therapy plan information in a memory (not illustrated) of the central control device 32. Since the central line of the irradiation head 4 is aligned with a certain single X-ray irradiation direction defined in the therapy plan, the central control device 32 outputs a rotation control command to the rotation gantry 2 so as to rotate the rotation gantry 2. The motor in the trestle 3 is driven in response to the rotation control command such that the rotation shaft 5 is rotated, and thus the rotation gantry 2 is rotated. When the central line of the irradiation head 4 is located in the X-ray irradiation direction, the motor is stopped, and thus rotation of the rotation gantry 2 is stopped.

The central control device 32 controls the variable collimator 11, and thus aligns a shape of an opening of the variable collimator 11 with a shape of the affected part viewed from the X-ray irradiation direction on the basis of the therapy plan information. The central control device 32 outputs an activation control command to the electron beam generation portion 7.

In the electron beam generation portion 7, a voltage is applied to a filament on the basis of the activation control command, and electrons are emitted from the heated filament. A plurality of emitted electrons form an electron beam, and are incident to the linear accelerator 8. The electron beam is accelerated by the linear accelerator 8, and thus becomes an electron beam having predetermined energy. An electron beam 36 emitted from the linear accelerator 8 has predetermined energy, and collides with the target 10 as a result of an advancing direction thereof being bent by the deflection electromagnet 9. The electron beam 36 collides with the target 10, and thus an X-ray 37 is emitted from the target 10. The X-ray 37 advances toward the affected part of the patient 35 on the bed 15 along the central line of the irradiation head 4, and is emitted from the irradiation head 4 so as to be applied to the affected part through the opening of the variable collimator 11.

The affected part is irradiated with the X-ray 37, and thus each radiation detector 21 of the radiation detection device 19 inserted into the body detects the X-ray 37. The applied X-ray 37 is incident to the light emitting portion 22 of the radiation detector 21. The periphery of the light emitting portion 22 is surrounded by the cover 23, and thus external light is blocked by the cover 23 and does not reach the light emitting portion 22. Thus, the photon p generated in the light emitting portion 22 is input to the photoelectric converter 26 through the core 24A of the optical fiber 24. The radiation detector 21 having the light emitting portion 22 made of Nd:YAG outputs a plurality of photons corresponding to total energy of a plurality of X-rays which are incident at one time, one by one with the time delay.

A single photon which is input to the photoelectric converter 26 is converted into a single electric pulse. Thus, the photoelectric converter 26 sequentially outputs electric pulses of the number corresponding to the number of input photons. The counting unit 27 to which the electric pulses are input counts the number of input electric pulses, and obtains the number of electric pulses per unit time, that is, a counting rate of the electric pulses. The obtained counting rate of the electric pulses is input to the dose rate calculation unit 28 from the counting unit 27.

The counting rate of the electric pulses corresponds to a photon counting rate on a one-to-one basis, and thus the dose rate calculation unit 24 converts the counting rate of the electric pulses into a dose rate by using the information of the data table (characteristics in FIG. 8) stored in the memory. The obtained dose rate is a dose rate at an insertion position of the radiation detector 21 inserted into the body of the patient, and is obtained for each radiation detector 21 inserted into the body.

Figure 4:
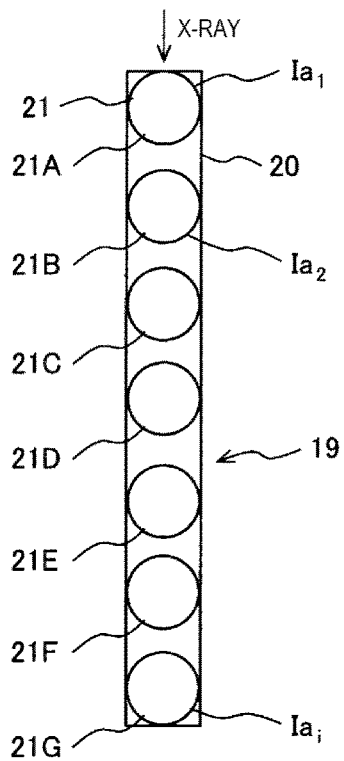
FIG. 4 is a sectional view taken along a line A-A in FIG. 3.

A description will be made of a dose rate $Ia_i$ (where i=1 to M (where M is the number of radiation detectors 21 included in the radiation detection device 19)) at each position of the seven radiation detectors 21 included in the radiation detection device 19, that is, the radiation detectors 21A, 21B, 21C, 21D, 21E, 21F, and 21G (refer to FIG. 4). In FIG. 4, it is assumed that the X-ray 37 is applied from the radiation detector 21A toward the radiation detector 21H in the body of the patient 35. The X-ray 37 transmitted through the radiation detector 21A is incident to the radiation detector 21B, and the X-ray 37 transmitted through the radiation detector 21B is incident to the radiation detector 21C. As mentioned above, the X-ray 37 transmitted through the radiation detector 21 located on the upstream side is incident to another radiation detector located directly on the downstream side of the radiation detector 21. Incidence and transmission of the X-ray 37 on the radiation detectors 21 are repeated, and, finally, the X-ray 37 transmitted through the radiation detector 21F is incident to the radiation detector 21G.

Figure 9:
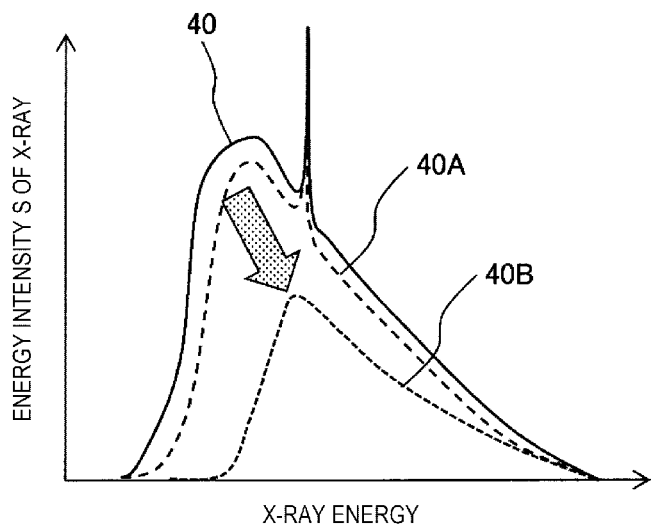
FIG. 9 is an explanatory diagram illustrating an example of an X-ray energy distribution used in the X-ray therapy apparatus.

The X-ray 37 incident to the radiation detector 21A gives energy of the X-ray 37 to each radiation detector 21 due to interaction with each radiation detector 21 whenever the X-ray is transmitted through each of the radiation detectors 21A to 21G arranged in a line. An energy distribution 40 of the X-ray 37 incident to the radiation detector 21A which is located on the most upstream side in the irradiation direction of the X-ray 37 is broad as illustrated in FIG. 9, and various energy levels are present in the energy distribution. An X-ray having relatively low energy is easily absorbed in a substance, and thus a low energy component of the X-ray 37 is reduced whenever the X-ray is transmitted through the radiation detector 21. Thus, as illustrated in FIG. 9, the energy distribution of the X-ray 37 changes whenever the X-ray 37 is transmitted through the radiation detector 21, such as an energy distribution 40A of the X-ray 37 transmitted through the radiation detector 21A, . . . , and an energy distribution 40B of the X-ray 37 transmitted through the radiation detector 21G. A dose rate Ia at the position of each radiation detector 21, obtained by the dose rate calculation unit 24 reflects such a change in the X-ray energy distribution therein.

Here, it is assumed that a dose rate at the position where the radiation detector 21A located on the most upstream side in the X-ray irradiation direction, obtained by the dose rate calculation unit 24, is $Ia_1$, a dose rate at the position where the radiation detector 21B is disposed is $Ia_2$, and a dose rate at the position where the radiation detector 21G located on the most downstream side is $Ia_1$, that is, $I_7$. It is assumed that a dose rate is $Ia_3$ at the position of the radiation detector 21C, a dose rate is $Ia_4$ at the position of the radiation detector 21D, a dose rate is $Ia_5$ at the position of the radiation detector 21E, and a dose rate is $Ia_6$ at the position of the radiation detector 21F. As described above, since, whenever the X-ray 37 is transmitted through the radiation detector 21, a low energy component of the X-ray 37 is reduced, and thus the intensity of the X-ray 37 is lowered, the dose rate has a relationship of $Ia_1 > Ia_2 > Ia_3 > Ia_4 > Ia_5 > Ia_6 > Ia_7$.

The dose rate at the position of each radiation detector 21 in the body, obtained by the dose rate measurement device 25, is input to the irradiation direction determination device 29 and the energy distribution analysis device 30. The irradiation direction determination device 29 determines an irradiation direction of the X-ray 37 applied into the body by using the input dose rate.

Figure 10A:
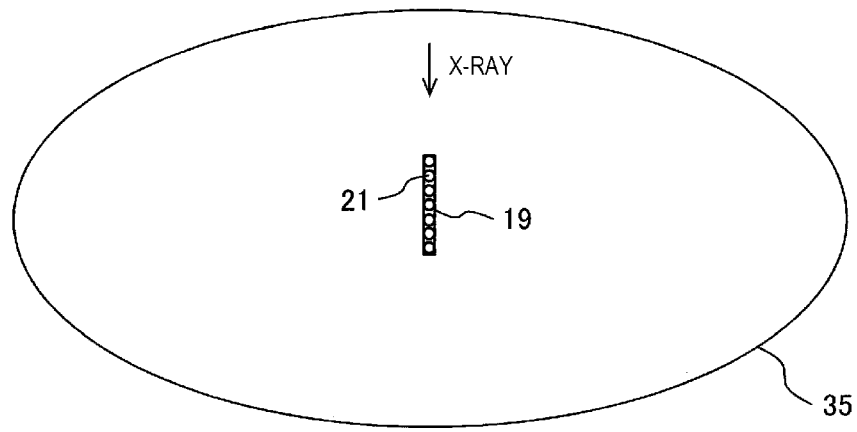
FIG. 10A is an explanatory diagram illustrating a state in which a string of a plurality of radiation detectors included in the radiation detection device illustrated in FIG. 3, inserted into the body, matches an X-ray irradiation direction.
Figure 10B:
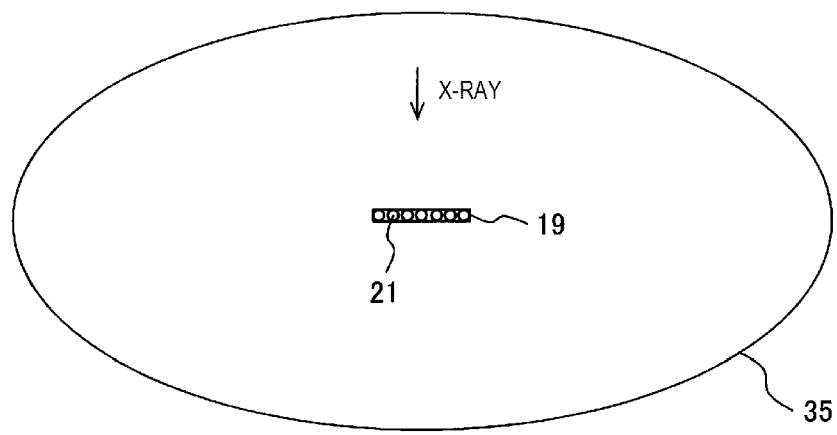
FIG. 10B is an explanatory diagram illustrating a state in which a string of a plurality of radiation detectors included in the radiation detection device illustrated in FIG. 3, inserted into the body, is orthogonal to the X-ray irradiation direction.
Figure 10C:
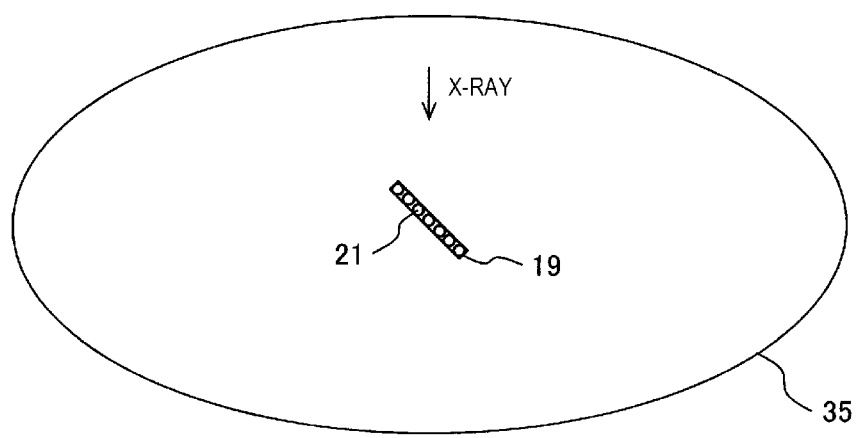
FIG. 10C is an explanatory diagram illustrating a state in which a string of a plurality of radiation detectors included in the radiation detection device illustrated in FIG. 3, inserted into the body, is inclined with respect to the X-ray irradiation direction.

In a case where the radiation detection device 19 is inserted into the body, there is a high probability that a direction of the radiation detection device 19 may be changed during the insertion. A principal direction of the radiation detection device 19 supposed in the body will be described with reference to FIGS. 10A, 10B, and 10C. In FIGS. 10A, 10B, and 10C, the X-ray 37 is assumed to be applied to the patient 35 in a direction of each arrow. For example, as in FIG. 10A, in a case where a linear string (hereinafter, simply referred to as a string of the radiation detectors 21) of a plurality of radiation detectors 21 (specifically, the radiation detectors 21A, 21B, 21C, 21D, 21E, 21F, and 21G) in the radiation detection device 19 matches the irradiation direction of the X-ray 37, an X-ray energy intensity at a position of the string of the radiation detectors 21 can be obtained. However, in a case where the string of the radiation detectors 21 in the radiation detection device 19 is disposed to be orthogonal to the irradiation direction of the X-ray 37 as in FIG. 10B, or is disposed to be inclined with respect to the irradiation direction of the X-ray 37 as in FIG. 10C, an X-ray energy intensity at a position of the string of the radiation detectors 21 cannot be obtained. It is hard to understand a direction in which the string of the radiation detectors 21 is directed in the radiation detection device 19 in advance from the outside of the patient 35.

Hereinafter, a description will be made of the reason why an X-ray energy intensity at a position of the string of the radiation detectors 21 cannot be obtained in cases where the string of the radiation detectors 21 is disposed to be orthogonal to the irradiation direction of the X-ray 37 and to be inclined with respect to the irradiation direction of the X-ray 37. In cases where the string of the radiation detectors 21 is orthogonal to the irradiation direction and is inclined with respect to the irradiation direction, the X-ray 37 having the energy distribution 40 illustrated in FIG. 9 is substantially equally incident to all of the radiation detectors 21 (the radiation detectors 21A to 21G) present in the string. In a case where X-rays having substantially identical energy distributions are detected in the radiation detectors 21A to 21G included in the string, simultaneous equations of Equation (1) which will be described later is not formed, and thus there is only one equation correlating a dose rate vector I and an X-ray energy intensity vector S with each other, and thus inverse problem analysis based on Equation (2) which will be described later cannot be performed.

In contrast, as illustrated in FIG. 10A, in a case where the string of the radiation detectors 21 matches the irradiation direction of the X-ray 37, when the X-ray is transmitted through each radiation detector 21 in the string, a part of the X-ray is absorbed by each radiation detector 21, and thus an energy distribution of the X-ray changes whenever the X-ray is transmitted through each radiation detector 21 included in the string. As a result, the respective radiation detectors 21 (radiation detectors 21A to 21G) included in the string detect an X-ray having different energy distributions. Since the respective radiation detectors 21 included in the string detect an X-ray having different energy distributions, simultaneous equations of Equation (1) which will be described later are formed, and thus inverse problem analysis based on Equation (2) which will be described later can be performed.

The inventors obtained a dose rate at a position of each radiation detector 21 included in the string of the radiation detectors 21 in each of a state in which the string of the radiation detectors 21 of the radiation detection device 19 is directed in the X-ray irradiation direction as illustrated in FIG. 10A, a state in which the string of the radiation detectors 21 is disposed to be orthogonal to the X-ray irradiation direction as illustrated in FIG. 10B, and a state in which the string of the radiation detectors 21 is disposed to be inclined with respect to the X-ray irradiation direction as illustrated in FIG. 10C. Such a dose rate was obtained on the basis of a radiation detection signal output from each radiation detector 21 when an X-ray generated by an X-ray tube device was applied to the radiation detection device 19.

When an X-ray from the X-ray tube device was applied, the radiation detection device 19 was disposed to face an X-ray emission port of the X-ray tube device such that the string of the radiation detectors 21 included in the radiation detection device 19 was brought into the states illustrated in FIGS. 10A, 10B, and 10C. As a result, in the state in which the string of the radiation detectors 21 was directed in the X-ray irradiation direction as illustrated in FIG. 10A, a dose rate profile 47 indicated by ● in FIG. 16 which will be described later was obtained by using a dose rate (a dose rate at a position of each radiation detector 21) obtained on the basis of an output signal from each radiation detector 21. The dose rate profile 47 is a reference dose rate profile used to determine whether or not the string of the radiation detectors 21 matches the X-ray irradiation direction. In the state in which the string of the radiation detectors 21 was disposed to be orthogonal to the X-ray irradiation direction as illustrated in FIG. 10B, a dose rate profile 49 indicated by ○ in FIG. 16 which will be described later was obtained by using a dose rate (a dose rate at a position of each radiation detector 21) obtained on the basis of an output signal from each radiation detector 21. In the state in which the string of the radiation detectors 21 was disposed to be inclined with respect to the X-ray irradiation direction as illustrated in FIG. 10C, a dose rate profile 48 indicated by ■ in FIG. 16 which will be described later was obtained by using a dose rate (a dose rate at a position of each radiation detector 21) obtained on the basis of an output signal from each radiation detector 21. In a state in which the string of the radiation detectors 21 was disposed to be inclined in a direction orthogonal to the string of the radiation detectors 21 illustrated in FIG. 10C, a dose rate profile 50 indicated by □ in FIG. 16 which will be described later was obtained by using a dose rate (a dose rate at a position of each radiation detector 21) obtained on the basis of an output signal from each radiation detector 21. Information regarding each dose rate profile is stored in a memory of the irradiation direction determination device 29.

The above-described reference dose rate profile and a reference dose rate distribution described in Example 3 are reference dose rate information.

The irradiation direction determination device 29 compares data regarding the dose rate which is input from the dose rate calculation unit 28 of each dose rate measurement device 25 with data regarding the dose rate profile stored in the memory, so as to determine an irradiation direction of the X-ray 37 applied into the body. In a case where each input dose rate matches the dose rate profile 47, the irradiation direction determination device 29 determines that the linear string of the radiation detectors 21A, 21B, 21C, 21D, 21E, 21F, and 21G of the radiation detection device 19 is directed in the irradiation direction of the X-ray 37. In a case where it is determined that the string of the radiation detectors 21 matches the irradiation direction of the X-ray 37, the irradiation direction determination device 29 outputs an analysis permission command to the energy distribution analysis device 30.

In a case where the string of the radiation detectors 21 does not match the irradiation direction of the X-ray 37, the irradiation direction determination device 29 outputs a rotation command to the drive control device 44 of the sensor insertion device 63 since the string of the radiation detectors 21 does not match the irradiation direction of the X-ray 37. The drive control device 44 having received the rotation command drives the motor of the first drive device 43A and the motor of the second drive device 43B, so as to rotate the inner shaft 42B and the outer shaft 42A. For example, in a case where each input dose rate matches the dose rate profile 48, the string of the radiation detectors 21 of the radiation detection device 19 is disposed as illustrated in FIG. 10C, and thus the string is inclined by 45° in the counterclockwise direction with respect to the irradiation direction of the X-ray 37. Thus, the drive control device 44 drives the motor of the first drive device 43A and the motor of the second drive device 43B such that the string of the radiation detectors 21 is rotated by 45° in the clockwise direction. When the string of the radiation detectors 21 is rotated by 45° in the clockwise direction, the motor of the first drive device 43A and the motor of the second drive device 43B are stopped. In this case, the string of the radiation detectors 21 matches the irradiation direction of the X-ray 37. Thus, the irradiation direction determination device 29 determines that the dose rate which is input from each dose rate measurement device 25 matches the dose rate profile 47, and outputs an analysis permission command to the energy distribution 40.

Figure 16:
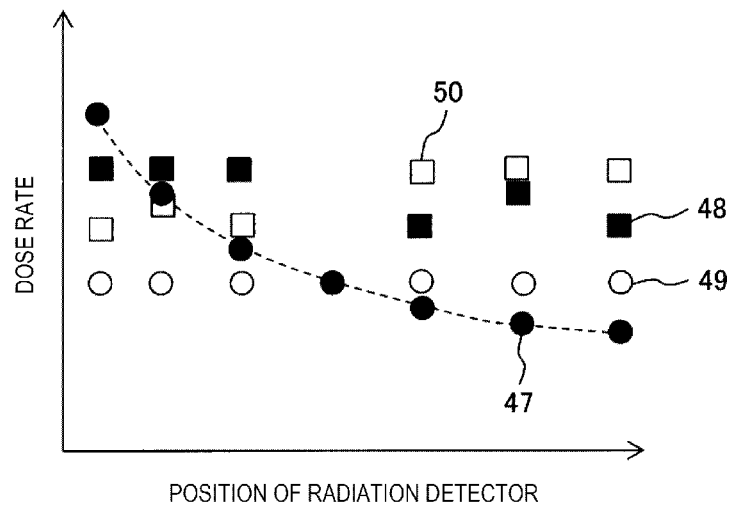
FIG. 16 is a characteristic diagram illustrating dose rates measured at positions of radiation detectors included in each radiation detector group illustrated in FIG. 15.
Figure 17:
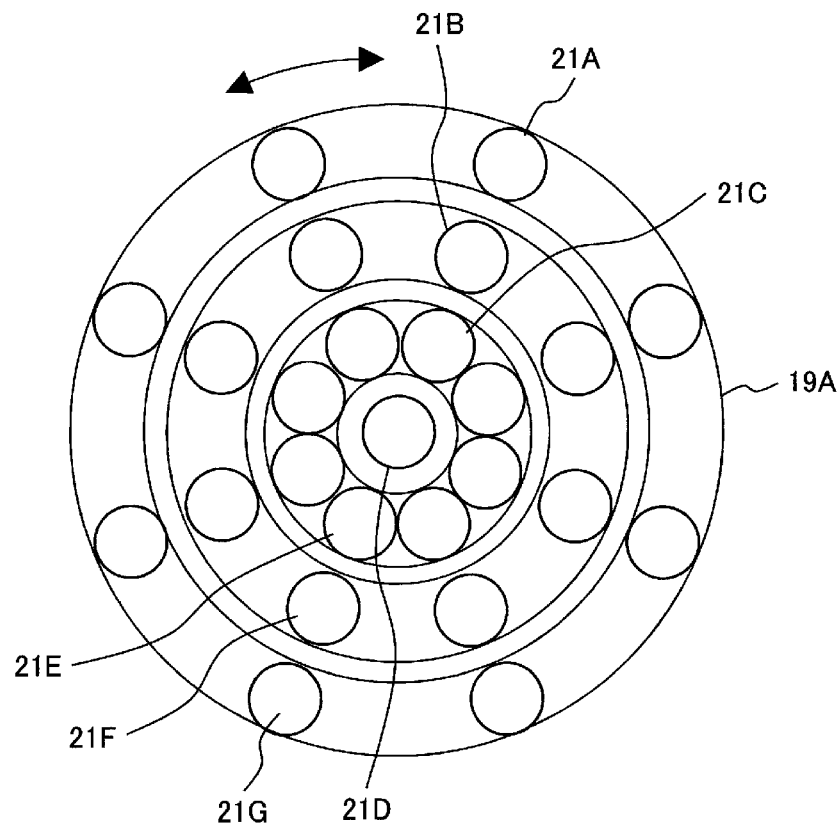
FIG. 17 is an explanatory diagram schematically illustrating a rotation state of the radiation detection device illustrated in FIG. 13.

Instead of a state in which the radiation detection device 19 disposed in front of the X-ray tube device is rotated by 45° as described above, in each state in which the radiation detection device 19 is rotated by, for example, 10°, an X-ray may be applied to the radiation detection device 19 from the X-ray tube device, and information regarding a dose rate profile as illustrated in FIG. 16 may be created in advance in each state by obtaining a dose rate at a position of each radiation detector 21 on the basis of an output signal from each radiation detector 21 of the radiation detection device 19. In a case where it is determined that a dose rate which is input from each dose rate measurement device 29 does not match the dose rate profile 47, the irradiation direction determination device 29 refers to the dose rate profile information in each state in which the radiation detection device 19 is rotated by 10°, and can thus more finely understand a rotation angle of the radiation detection device 19 using the sensor insertion device 63 in order to match the string of the radiation detectors 21 with the irradiation direction of the X-ray 37.

The energy distribution analysis device 30 having received the analysis permission command receives the dose rate at the position of each radiation detector 21 in the body, obtained by each dose rate measurement device 25, and obtains an X-ray energy distribution in the affected part of the patient 35 irradiated with the X-ray 37 through analysis by using the dose rate. Hereinafter, a description will be made of a summary of analysis of obtaining an X-ray energy distribution.

Figure 11:
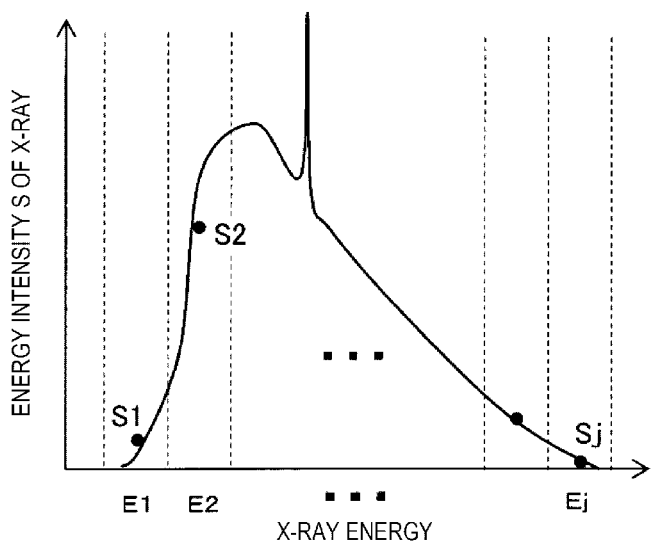
FIG. 11 is an explanatory diagram illustrating an example of division of an X-ray energy range and an X-ray energy intensity in each region.

In a case where an X-ray energy distribution is obtained, an energy range of the X-ray 37 applied to the affected part is divided into a plurality of regions. The energy range of the X-ray 37 is divided into regions $E_1, E_2, \ldots,$ and $E_j$ (where j=1 to N) as illustrated in FIG. 11. N is the number of separate regions. Herein, an X-ray energy intensity corresponding to each region $E_j$ is indicated by $S_j$. A single energy intensity $S_j$ is obtained for each region $E_j$ as a result of X-ray energy distribution analysis. A width of a separate region and the number of separate regions are determined by an operator. Widths of a plurality of separate regions may or not be the same as each other. More preferably, in a portion where a change ratio of an X-ray intensity to X-ray energy is high, a width of a separate region may be set to be small.

In Equations (1), (2), (3), and (4), I is a dose rate vector, S is an X-ray energy intensity vector, and R is a response matrix. In energy distribution analysis performed by the energy distribution analysis device 30, an energy distribution is obtained by applying one technique of inverse problem analysis called an unfolding method on the basis of Equation (2) by using Equation (1) expressed by the dose rate vector I, the energy intensity vector S, and the response matrix R correlating the vectors with each other.

$$I = R \times S \quad (1)$$

$$S = R^{-1} \times I \quad (2)$$

Here, the dose rate vector I is expressed as in Equation (3), the energy intensity vector S is expressed as in Equation (4), and the response matrix R is expressed as in Equation (5).

$$I = (Ia_1, \cdots, Ia_i)^T \quad (3)$$

$$S = (S_1, \cdots, S_j)^T \quad (4)$$

$$R = \begin{pmatrix} R_{11} & \cdots & R_{1j} \\ \vdots & & \vdots \\ R_{i1} & \cdots & R_{ij} \end{pmatrix} \quad (5)$$

The response matrix R is obtained in advance through simulation. In the simulation for obtaining the response matrix R, a technique of analyzing a behavior of a radiation particle according to a Monte Carlo method may be used. Representatives of simulation codes based on the Monte Carlo method are MCNP and PHITS. MCNP is a general-purpose Monte Carlo N-Particle code that can be used for neutron, photon, or electron transport, developed in Los Alamos National Laboratory of U.S.A. PHITS is a particle/heavy ion behavior analysis code, and is a general-purpose Monte Carlo computation code enabling a radiation behavior in a three-dimensional system having any shape to be analyzed, developed in Japan. Simulation using simulation codes based on the Monte Carlo method is performed by matching a relative positional relationship of a detector, a radiation source, a human body, and the like with an actually supposed positional relationship. The response matrix R is computed in advance through such simulation.

In the energy distribution analysis device 30, the response matrix R which is expressed in Equation (5) and is computed in advance is assigned to Equation (2), and thus the X-ray energy intensity $S_j$ (where j=1 to N) is obtained on the basis of the dose rate $Ia_i$ (where i=1 to 7) measured at the position of each dose calculation device 21 of the radiation detection device 19 inserted into the body. Information regarding the energy intensity obtained by the energy distribution analysis device 30, that is, the energy intensities $S_1, S_2, \ldots,$ and $S_7$ are displayed on a display device (not illustrated). The energy distribution analysis device 30 obtains a dose on the basis of the obtained X-ray energy intensities $S_1, S_2, \ldots,$ and $S_7$ which are energy distribution information.

The dose obtained by the X-ray energy distribution measurement apparatus 62 is input to the central control device 32. The central control device 32 outputs a stop control command to the electron beam generation portion 7 when a dose (the dose obtained by the X-ray energy distribution measurement apparatus 62) applied to the affected part becomes a set dose which is input from the database 33 due to irradiation with the X-ray 37 on the affected part of the patient 35 on the bed 15. As a result, generation of an electron beam in the electron beam generation portion 7 is stopped, and irradiation with an X-ray on the affected part is stopped. A dose may be obtained by the central control device 32 by using the X-ray energy intensities $S_1, S_2, \ldots,$ and $S_7$ which are input from the X-ray energy distribution measurement apparatus 62.

Multiple-field irradiation with the X-ray 37 on the affected part of the patient 35 may be performed by matching the central line of the irradiation head 4 with another X-ray irradiation direction through rotation of the rotation gantry 2 as necessary.

According to the present example, since the radiation detection device 19 including a plurality of (seven) radiation detectors 21 linearly arranged in a line is used, even in a case where the radiation detection device 19 is inserted into the body, it is possible to determine whether or not the string of the plurality of radiation detectors 21 linearly arranged is directed in the irradiation direction of the X-ray 37, by using a dose rate at a position of each radiation detector 21, obtained by the dose rate measurement device 25 on the basis of an X-ray detection signal (photon) output from each radiation detector 21.

In a case where the string of the plurality of radiation detectors 21 linearly arranged is not directed in the irradiation direction of the X-ray 37, the radiation detection device 19 can be rotated by using the sensor insertion device 63, and thus the string of the radiation detectors 21 can be easily matched with the irradiation direction of the X-ray 37.

In the present example, in a state in which the string of the radiation detectors of the radiation detection device 19 matches the irradiation direction of the X-ray 37, each radiation detector 21 detects the X-ray 37 applied to the affected part of the patient 35 on the bed 15 from the irradiation head 4, and the dose rate measurement device 25 obtains the dose rate $Ia_i$ (where i=1 to 7) at the position of each dose calculation device 21 inserted into the body on the basis of an X-ray detection signal (photon) output from the radiation detector 21. An energy intensity in the affected part, that is, the energy intensity $S_j$ (where j=1 to N) at the position of the radiation detection device 19 is obtained by using each dose rate $Ia_i$ obtained in the above-described way, and thus it is possible to measure an energy distribution in the vicinity of the affected part irradiated with the X-ray 37 with high accuracy. In other words, it is possible to monitor an energy distribution of the body irradiated with the X-ray 37 with high accuracy by using the X-ray energy distribution measurement apparatus 62.

Since the energy intensity $S_j$ (where j=1 to 7) in the affected part is obtained by using the dose rate $Ia_i$ at the position of each radiation detector 21 inserted into the body, the X-ray 37 which is transmitted through one or a plurality of radiation detectors 21 located on the upstream side in the X-ray irradiation direction and of which energy is attenuated is incident to the radiation detectors 21B, 21C, 21D, 21E, 21F, and 21G except for the radiation detector 21A located on the most upstream side in the X-ray irradiation direction among the respective radiation detectors 21. Thus, the obtained dose rate $Ia_i$ at the position of each of the radiation detectors 21B, 21C, 21D, 21E, 21F, and 21G has a value in which the attenuation of the energy is reflected. Therefore, in the X-ray energy distribution measurement apparatus 62, the energy intensity $S_j$ is obtained by using the dose rate $Ia_i$, and, thus, according to the present example, it is possible to obtain a more highly accurate energy distribution in the body.

In the present example, since a dose rate at the position of each dose calculation device 21 is obtained on the basis of an output signal from each radiation detector 21 included in the string of the radiation detectors 21 of the radiation detection device 19 inserted into the body, it is possible to estimate to what extent the string of the radiation detectors 21 is deviated relative to the irradiation direction of the X-ray 37. Specifically, a dose rate at the position of each radiation detector 21 included in the string of the radiation detectors 21 is compared with the dose rate profiles 47, 48, 49, and 50 illustrated in FIG. 16 which will be described later, and thus it is possible to understand to what extent the string of the radiation detectors 21 is deviated relative to the irradiation direction of the X-ray 37. In the present example, in a case where the string of the radiation detectors 21 illustrated in FIG. 16 is deviated relative to the irradiation direction of the X-ray 37, a dose rate profile closest to a profile of the dose rate at the position of each radiation detector 21 included in the string of the radiation detectors 21 is compared with the dose rate profile 47 which is a reference dose rate profile, and thus it is possible to understand an approximate deviation angle. Thereafter, the radiation detection device 19 is rotated by the sensor insertion device 63 on the basis of the understood deviation angle. As mentioned above, in a case where the string of the radiation detectors 21 is deviated relative to the irradiation direction of the X-ray 37, the string of the radiation detectors 21 can be matched with the irradiation direction of the X-ray 37 within a shorter period of time.

In JP-A-2007-114067, a scintillator layer is formed on an inner surface of each of two optical fibers which are disposed in parallel and to which X-rays are incident, and, when an X-ray transmitted through one optical fiber is incident to the other optical fiber, information regarding a radiation flying direction is generated on the basis of a signal output from the scintillator layer of each optical fiber. In JP-A-2007-114067, the information regarding a flying direction is created on the basis of, for example, an incidence time point at which radiation is incident to each optical fiber, or on the basis of a time point at which an optical signal output from each scintillator layer reaches photoelectric conversion means separately connected to each optical fiber. In JP-A-2007-114067, it is not possible to understand to what extent the string of the radiation detectors 21 is deviated relative to the irradiation direction of the X-ray 37 unlike the present example.

According to the present example, since the radiation detection device 19 including a plurality of radiation detectors 21 is inserted into the body, it is possible to measure dose rates at positions where the radiation detectors 21 are disposed in an affected part irradiated with an X-ray and in the vicinity of the affected part.

Since the light emitting portion 22 of the radiation detector 21 used in the present example is made of, for example, a radiation light emitting material containing a rare earth element in a base material such as transparent YAG, a counting rate of photons output from the light emitting portion 22 of the radiation detector 21 is proportional to a dose rate in a wide range, for example, a dose rate in a range of a dose rate of $1.0 \times 10^{-2}$ to $1.0 \times 10^5$ Gy/h as illustrated in FIG. 8. The light emitting portion 22 can output a plurality of photons corresponding to total energy of a plurality of X-rays which are incident at one time, one by one with the time delay. Thus, each photon can be converted into each electric pulse, and thus a dose rate can be obtained with high accuracy.

Figure 12:
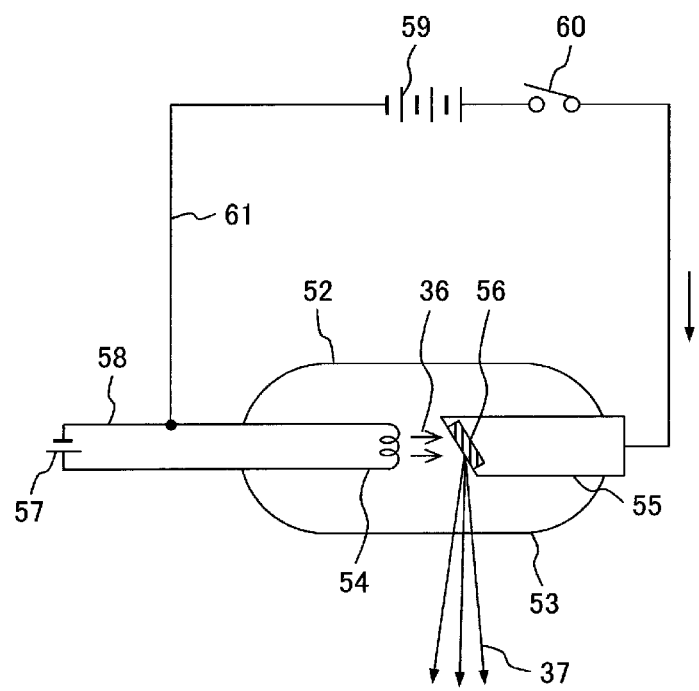
FIG. 12 is a configuration diagram illustrating an example of an X-ray tube device.

In the X-ray therapy apparatus 1, the X-ray generation device 6 is used, but an X-ray tube device may be used instead of the X-ray generation device 6. A description will be made of an X-ray tube device 52 which is an example of the X-ray tube device with reference to FIG. 12. The X-ray tube device 52 includes an anode 55 and a filament 54 disposed in a glass tube 53. The inside of the glass tube 53 is a vacuum atmosphere, and the anode 55 faces the filament 54. A target 56 is attached to a surface of the anode 55 facing the filament 54. The target 56 is attached to the anode 55 in a tilted state. A power source 57 is connected to the filament 54 via a wire 58, and a high voltage power source 59 is connected to the anode 55 and the wire 58 via a wire 61. A switch 60 is provided at the wire 61.

The X-ray tube device 52 is installed at the arm portion of the rotation gantry 2 instead of the X-ray generation device 6 in the X-ray therapy apparatus 1. A current flows from the power source 57 to the filament 54 which is a cathode, and, in a case where the switch 60 is closed in a state in which the filament 54 is heated such that a high voltage from the high voltage power source 59 is applied between the filament 54 and the anode 55, an electron beam 36 generated from the filament 54 collides with the target 56 at a high speed. An X-ray 37 is generated from the target 56 due to the collision of the electron beam 36 with the target 56. The X-ray 37 advances along the central line of the irradiation head 4, and is emitted to the variable collimator 11 from the irradiation head 4 so as to be applied to the affected part of the patient 35 on the bed 15. Even if the X-ray tube device 52 is used as mentioned above, irradiation with an X-ray can be performed on the affected part. The X-ray tube device 52 may be used instead of the X-ray generation device 6 in an X-ray therapy apparatus 1A of Example 2 and an X-ray therapy apparatus 1B of Example 3 which will be described later.

Example 2

Figure 13:
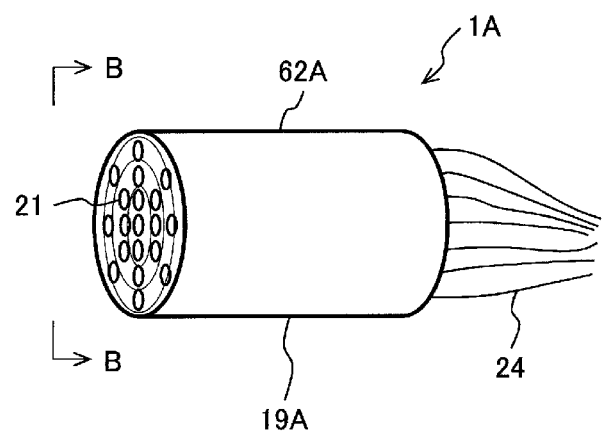
FIG. 13 is a configuration diagram of a radiation detection device used in an X-ray therapy apparatus of Example 2 which is another preferable example of the present invention.

An X-ray therapy apparatus of Example 2 which another preferable example of the present invention will be described with reference to FIGS. 13 and 14.

An X-ray therapy apparatus 1A of the present example has a configuration in which the X-ray energy distribution measurement apparatus 62 is replaced with an X-ray energy distribution measurement apparatus 62A in the X-ray therapy apparatus 1 of Example 1. Other configurations of the X-ray therapy apparatus 1A are the same as those of the X-ray therapy apparatus 1. The X-ray energy distribution measurement apparatus 62A has a configuration in which the radiation detection device 19 is replaced with a radiation detection device 19A illustrated in FIGS. 13 and 14 in the X-ray energy distribution measurement apparatus 62. Other configurations of the X-ray energy distribution measurement apparatus 62A are the same as those of the X-ray energy distribution measurement apparatus 62.

Figure 14:
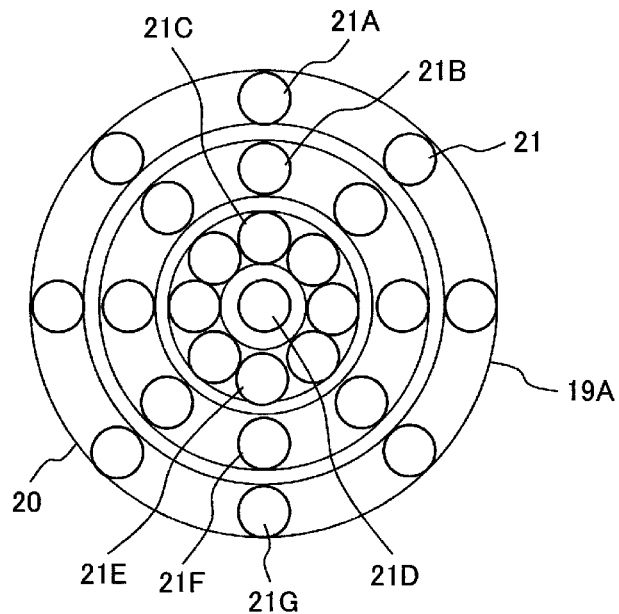
FIG. 14 is a sectional view taken along a line B-B in FIG. 13.

A plurality of radiation detectors 21 included in the radiation detection device 19A are disposed concentrically and radially centering on the radiation detector 21 disposed at the central axis of the radiation detection device 19A, specifically, the radiation detector 21D, as illustrated in FIG. 14. Due to this arrangement, three deterioration rings each including eight radiation detectors 21 are present concentrically around the radiation detector 21D located at the center. The radiation detectors 21 are attached to the support member 20 in the same manner as in the radiation detection device 19 used in Example 1. The optical fiber 24 connected to the light emitting portion 22 of each radiation detector 21 is connected to the photoelectric converter 26 of the separate dose rate measurement device 25.

Figure 15:
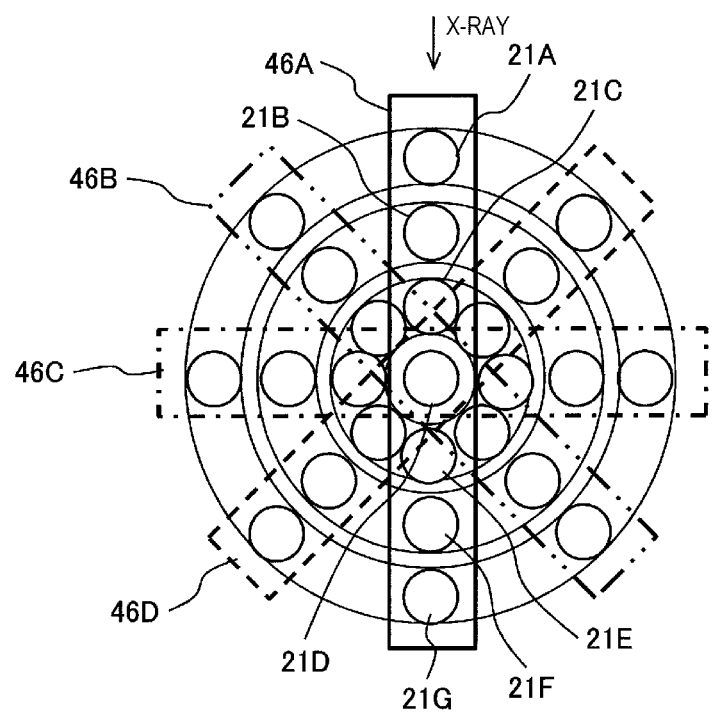
FIG. 15 is an explanatory diagram illustrating a plurality of radiation detector groups in the radiation detection device illustrated in FIG. 13, including a plurality of radiation detectors which are arranged in a line through grouping.

The plurality of radiation detectors 21 disposed concentrically and radially may be grouped into four detector groups such as detector groups 46A, 46B, 46C, and 46D as illustrated in FIG. 15. The radiation detector 21D disposed at the central axis of the radiation detection device 19A is included in each detector group. For example, the detector group 46A includes seven radiation detectors 21 arranged linearly in a line, that is, radiation detectors 21A, 21B, 21C, 21D, 21E, 21F, and 21G. Similarly, each of the remaining detector groups 46B, 46C, and 46D also includes seven radiation detectors 21 arranged linearly in a line.

The radiation detector 21D included in each of strings of the radiation detectors of the four deterioration groups is included in all of the strings of the radiation detectors, and is thus shared by the strings of the radiation detectors. The radiation detector 21D is disposed at the central axis of the radiation detection device 19A. The strings of the radiation detectors of the detector groups 46A, 46B, 46C, and 46D are disposed at an interval of 45° centering on the radiation detector 21D, specifically, the central axis of the radiation detection device 19A. The radiation detection device 19A has the four detector groups. The radiation detection device 19 used in Example 1 has a single detector group including the seven radiation detectors 21 arranged linearly in a line.

A diameter of each of the radiation detectors 21 and the optical fibers 24 is 1 mm in the same manner as in Example 1. A diameter of the radiation detection device 19A used in the present example is less than 1 cm. The radiation detection device 19A is inserted into the body of the patient 35 through the mouth or the nostrils, or through the anus, in the same manner as the radiation detection device 19.

The inventors disposed the radiation detection device 19A in front of an X-ray tube device such that the detector group 46A thereof was directed in an irradiation direction of an X-ray, and applied an X-ray from the X-ray tube device to the radiation detection device 19A. As a result, a dose rate at a position of each radiation detector 21 of each detector group obtained on the basis of an output signal from each radiation detector 21 included in each of the detector groups 46A, 46B, 46C, and 46D is illustrated in FIG. 16. A dose rate distribution of the dose rate profile 47 was obtained in the detector group 46A, and a dose rate distribution of the dose rate profile 48 was obtained in the detector group 46B.

A dose rate distribution of the dose rate profile 49 was obtained in the detector group 46C, and a dose rate distribution of the dose rate profile 50 was obtained in the detector group 46D. Information regarding each of the dose rate profiles 47 to 50 is stored in a memory of the irradiation direction determination device 29 of the X-ray therapy apparatus 1A.

Typically, it is known that an X-ray is attenuated exponentially depending on a therapy of an object through which the X-ray is transmitted. Since the detector group 46A is directed in the X-ray irradiation direction, dose rates at the respective positions of the seven radiation detectors 21 arranged linearly in a line, included in the detector group 46A, are attenuated exponentially as in the dose rate profile 47 indicated by a dotted line as illustrated in FIG. 16. In a case where the respective dose rates in a single string of the radiation detectors 21 of the radiation detection device 19A match the dose rate profile 47, it is determined that the string of the radiation detectors 21 is directed in the X-ray irradiation direction. A direction from which an X-ray is incident to the detector group can be determined. Among positions of the radiation detectors 21 included in the string, the X-ray is applied from the radiation detector 21 located at a position where a dose rate is highest toward the radiation detector 21 located at a position where a dose rate is lowest.

There is a case where an X-ray irradiation direction may be present, for example, between the detector group 46A and the detector group 46B. In this case, a dose rate distribution for a certain single detector group of the radiation detection device 19A has a profile similar to the dose rate profile 47 and the dose rate profile 48, and, thus, it is determined that an X-ray irradiation direction is present between the detector group 46A causing the dose rate profile 47 and the detector group 46B causing the dose rate profile 48 in the state illustrated in FIG. 15.

A description will be made of cancer therapy of a patient using the X-ray therapy apparatus 1A. The patient 35 subjected to the X-ray therapy is placed on the bed 15 of the therapy table 12 in the same manner as in Example 1. The radiation detection device 19A is inserted into the body of the patient 35, and is located in the vicinity of an affected part. The X-ray 37 generated from the X-ray generation device 6 provided in the arm portion of the rotation gantry 2 of the X-ray therapy apparatus 1A is applied to the affected part which is positioned with respect to the central line of the irradiation head 4.

Each radiation detector 21 of the radiation detection device 19A inserted into the body detects the applied X-ray 37, and outputs a photo from the light emitting portion 22 thereof. The dose rate measurement device 25 separately connected to each light emitting portion 22 receives the photon and outputs a dose rate, as described in Example 1. The irradiation direction determination device 29 to which the dose rate output from each dose rate measurement device 25 is input compares the dose rate with information regarding each dose rate profile stored in the memory. In a case where the input dose rate for a certain string of the radiation detectors matches the dose rate profile 47, the irradiation direction determination device 29 determines that a detector group (for example, the detector group 46B) including the string of the radiation detectors is directed in the irradiation direction of the X-ray 37. In a case where there is no input dose rate group matching the dose rate profile 47, the irradiation direction determination device 29 determines that no strings of the radiation detectors of the detector groups match the irradiation direction of the X-ray 37. In this case, an operator compares a distribution of the respective input dose rates with information regarding each dose rate profile (for example, profile information illustrated in FIG. 16), displayed on a display device (not illustrated), and finds a distribution of the input dose rates located between pieces of profile information adjacent to each other (for example, between the dose rate profile 47 and the dose rate profile 48). In a case where there is such a distribution of the dose rates, in order to match a string of the radiation detectors of a detector group causing the dose rate distribution with the irradiation direction of the X-ray 37, the radiation detection device 19A inserted into the body is rotated by using the sensor insertion device 63. Due to this rotation, dose rates at positions of the radiation detectors 21, obtained on the basis of output signals from the respective radiation detectors 21 included in the string of the radiation detectors of the detector group, match the dose rate profile 47. As a result, the detector group matches the irradiation direction of the X-ray 37.

In a case where it is determined that a string of radiation detectors of a single detector group matches the irradiation direction of the X-ray 37, the energy distribution analysis device 30 receives an analysis permission command from the irradiation direction determination device 29, and performs the analysis described in Example 1 by using a dose rate at a position of each radiation detector 21 included in the string of the radiation detectors of the detector group matching the irradiation direction of the X-ray 37, obtained by each dose rate measurement device 25, so as to obtain the X-ray energy intensities $S_1$, $S_2$, . . . at a position of the deterioration group. The obtained X-ray energy is displayed on the display device.

The present example can achieve each effect achieved by Example 1. The present example uses the radiation detection device 19A including a plurality of detector groups in which the radiation detectors 21 are radially disposed. Therefore, in the present example, compared with Example 1 using the radiation detection device 19, a string of radiation detectors of a certain single detector group included in the radiation detection device 19A can be matched with an irradiation direction of the X-ray 37 at a small rotation angle of the radiation detection device 19A, and thus it is possible to reduce the time required to specify the irradiation direction of the X-ray 37. Consequently, it is possible to reduce the therapy time required for each patient and thus to improve throughput.

Example 3

Figure 18:
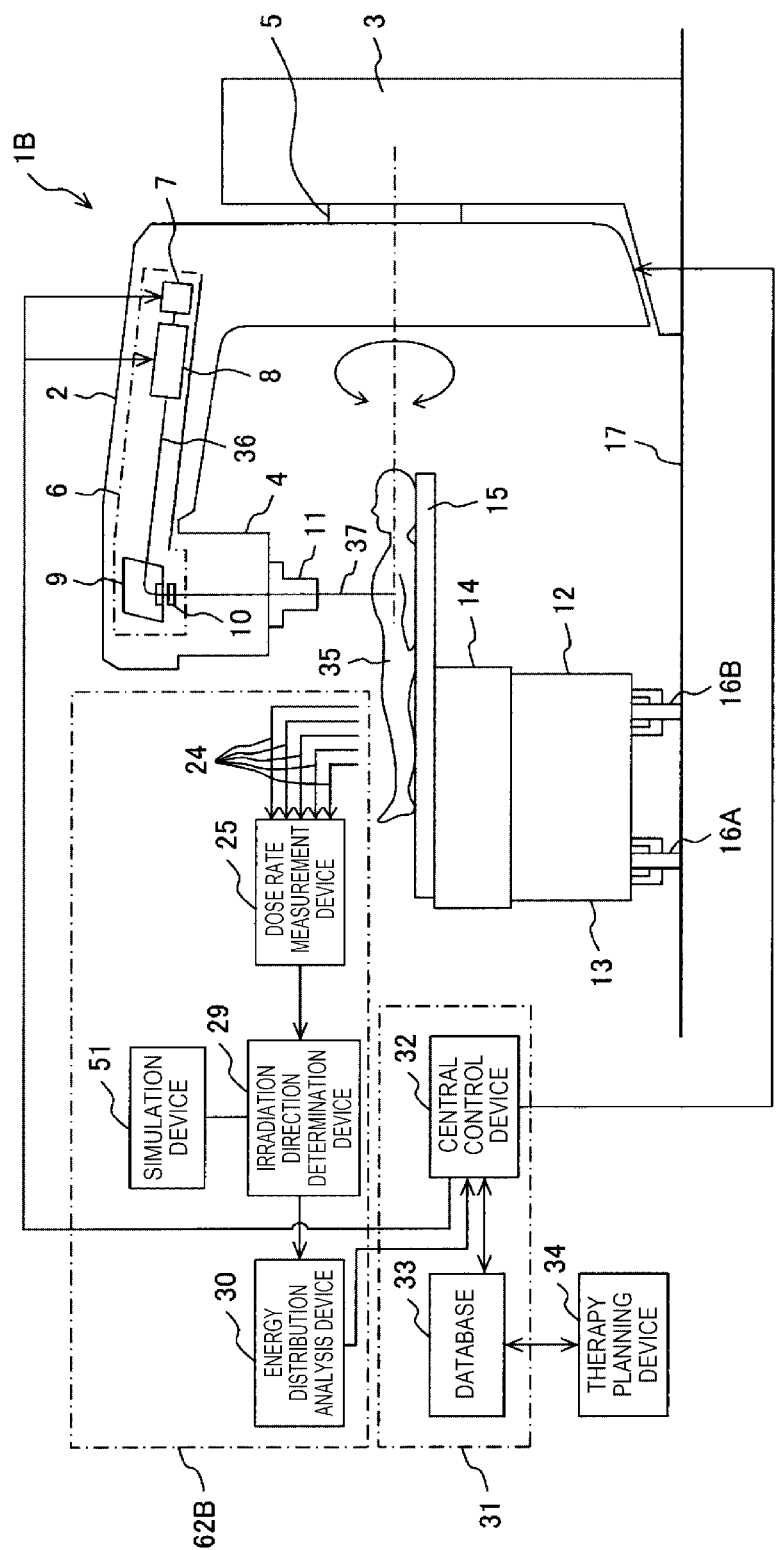
FIG. 18 is a configuration diagram of an X-ray therapy apparatus of Example 3 which is still another preferable example of the present invention.

An X-ray therapy apparatus of Example 3 which still another preferable example of the present invention will be described with reference to FIG. 18.

An X-ray therapy apparatus 1B of the present example has a configuration in which the X-ray energy distribution measurement apparatus 62 is replaced with an X-ray energy distribution measurement apparatus 62B in the X-ray therapy apparatus 1 of Example 1. Other configurations of the X-ray therapy apparatus 1A are the same as those of the X-ray therapy apparatus 1. The X-ray energy distribution measurement apparatus 62B has a configuration in which a simulation device 51 is added to the X-ray energy distribution measurement apparatus 62. Other configurations of the X-ray energy distribution measurement apparatus 62A except for the simulation device 51 are the same as those of the X-ray energy distribution measurement apparatus 62. The simulation device 51 is connected to the irradiation direction determination device 29. However, the X-ray therapy apparatus 1B uses the radiation detection device 19A used in Example 2 as a radiation detection device. The radiation detection device 19 may be used as a radiation detection device.

The simulation device 51 calculates a dose rate distribution for each of the detector groups 46A to 46D through simulation by using a system simulating the radiation detection device 19A. In the simulation device 51, MCNP or PHITS of simulation codes based on the Monte Carlo method is used to calculate a dose rate. Simulation for obtaining a dose rate for each detector group, using the simulation device 51, is preferably performed before the patient 35 subjected to X-ray therapy is irradiated with the X-ray 37 from the irradiation head 4, preferably, before the patient 35 is placed on the 15 and after a radiation detection device to be inserted into the body is determined.

Figure 19:
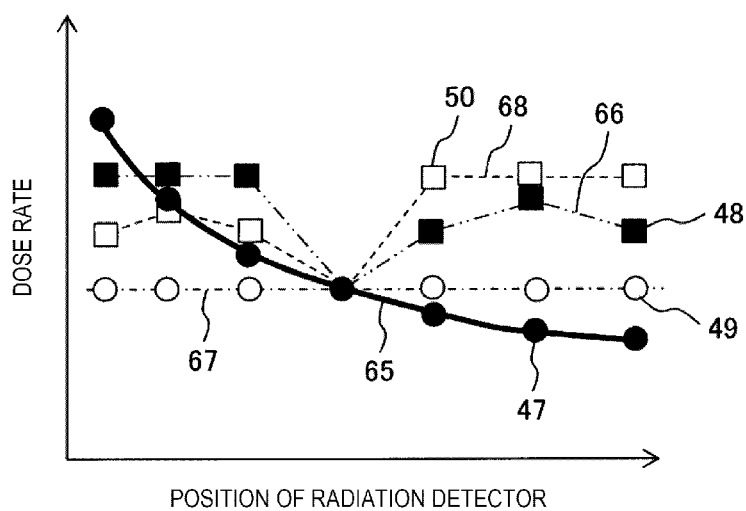
FIG. 19 is a characteristic diagram illustrating a dose rate at a position of each radiation detector, obtained through simulation performed by a simulation device illustrated in FIG. 18.

A dose rate distribution obtained through simulation using the simulation device 51 will be described with reference to FIG. 19. The simulation was performed assuming that the detector group 46A of the radiation detection device 19A was directed in the irradiation direction of the X-ray 37. In FIG. 19, a dose rate distribution 65 indicated by a solid line indicates a dose distribution in the detector group 46A, a dose rate distribution 66 indicated by a two-dot chain line indicates a dose distribution in the detector group 46B, a dose rate distribution 67 indicated by a dot chain line indicates a dose distribution in the detector group 46C, and a dose rate distribution 68 indicated by a dotted line indicates a dose distribution in the detector group 46D. Information regarding each of the dose rate distributions 65 to 68 obtained through the simulation is stored in the memory of the irradiation direction determination device 29.

FIG. 19 illustrates profiles of dose rates obtained on the basis of signals output from the respective radiation detectors 21 included in each detector group by applying X-rays from the X-ray tube device to the radiation detection device 19A in a state in which the detector group 46A of the radiation detection device 19A disposed in front of the X-ray tube device is directed in the X-ray irradiation direction. A dose rate profile 47 of the detector group 46A indicated by ●, a dose rate profile 48 of the detector group 46B indicated by ■, a dose rate profile 49 of the detector group 46C indicated by ○, and a dose rate profile 50 of the detector group 46D indicated by □ are illustrated.

The dose rate distribution 65 obtained through the simulation using the simulation device 51 matches the dose rate profile 47 obtained by detecting an applied X-ray. Similarly, the dose rate distribution 66 obtained through the simulation matches the dose rate profile 48 obtained by detecting an X-ray, the dose rate distribution 67 obtained through the simulation matches the dose rate profile 49 obtained by detecting an X-ray, and the dose rate distribution 68 obtained through the simulation matches the dose rate profile 50 obtained by detecting an X-ray.

FIG. 19 illustrates a dose rate simulation result assuming that the detector group 46A matches the X-ray irradiation direction, but simulation for a dose rate distribution in a case where each of the other detector groups 46B, 46C, and 46D matches the X-ray irradiation direction and simulation in a case where the X-ray irradiation direction is present between detector groups adjacent to each other are also performed. The simulation in a case where the X-ray irradiation direction is present between detector groups adjacent to each other is performed a plurality of times assuming that a gap between the detector groups adjacent to each other is divided into equal parts and the X-ray irradiation direction is present in each separate direction. Information regarding each dose rate distribution obtained through the simulation is also stored in the memory of the irradiation direction determination device 29.

A description will be made of cancer therapy of a patient using the X-ray therapy apparatus 1B. The radiation detection device 19A is inserted into the body of the patient 35 subjected to the X-ray therapy on the bed 15, and is located in the vicinity of an affected part. The X-ray 37 generated from the X-ray generation device 6 provided in the arm portion of the rotation gantry 2 of the X-ray therapy apparatus 1A is applied to the affected part which is positioned with respect to the central line of the irradiation head 4.

Each radiation detector 21 of the radiation detection device 19A inserted into the body detects the applied X-ray 37, and outputs a photo from the light emitting portion 22 thereof. The dose rate measurement device 25 separately connected to each light emitting portion 22 receives the photon and outputs a dose rate, as described in Example 1. The irradiation direction determination device 29 to which the dose rate output from each dose rate measurement device 25 is input compares the dose rate with information regarding each dose rate profile stored in the memory. In a case where each dose rate for a string of the radiation detectors 21 of a certain single detector group matches the dose rate distribution 65 which is a reference dose rate distribution, the irradiation direction determination device 29 determines that a detector group (for example, the detector group 46B) including the string of the radiation detectors is directed in the irradiation direction of the X-ray 37. In a case where the dose rate distribution 65 does not match each dose rate for a string of the radiation detectors 21 of any detector group, and it is determined that the irradiation direction of the X-ray 37 is present between any detector groups, for example, the detector group 46A and the detector group 46B, the irradiation direction determination device 29 obtains angle information regarding to what extent the irradiation direction of the X-ray 37 is deviated relative to the detector group 46A and the detector group 46B on the basis of simulation conditions. The drive control device 44 drives the first drive device 43A and the second drive device 43B of the sensor insertion device 63 on the basis of the angle information obtained by the irradiation direction determination device 29, so as to rotate the radiation detection device 19A, so that the detector group 46A or the detector group 46B is matched with the irradiation direction of the X-ray 37.

Thereafter, the energy distribution analysis device 30 performs the analysis described in Example 1, specifically, assigns the response matrix R which is expressed in Example (5) and is computed in advance to Equation (2) by using a dose rate at a position of each radiation detector 21 included in the string of the radiation detectors of the detector group matching the irradiation direction of the X-ray 37, obtained by each dose rate measurement device 25, so as to obtain the X-ray energy intensities $S_1, S_2, \ldots$ at a position of the deterioration group. In other words, an X-ray energy distribution in the affected part irradiated with the X-ray 37 is obtained.

The present example can achieve each effect achieved by Example 1. In the present example, it is possible to perform simulation in a case where an irradiation direction of the X-ray 37 is located between detector groups adjacent to each other by using the simulation device 51, and thus to more easily understand by what angle a string of radiation detectors of a detector group is deviated relative to the irradiation direction of the X-ray 37 than in Example 2. Thus, it is possible to reduce the therapy time required for each patient more than in Example 2.

REFERENCE SIGNS LIST 1, 1A, and 1B: X-ray therapy apparatus
2: rotation gantry
4: irradiation head
11: variable collimator
6: X-ray generation device
7: electron beam generation portion
8: linear accelerator
10: target
15: bed
19, 19A, and 19B: radiation detection device
21, and 21A to 21G: radiation detector
22: light emitting portion
24: optical fiber
25: dose rate calculation device
27: counting unit
28: dose rate calculation unit
29: irradiation direction determination device
30: energy distribution analysis device
31: control system
32: central control device
34: therapy planning device
41: sensor insertion system
42A: outer shaft
42B: inner shaft
43A: first drive device
43B: second drive device
44: drive control device
46A to 46D: detector group
51: simulation device
62, 62A, and 62B: X-ray energy distribution measurement apparatus
63: sensor insertion device

The invention claimed is:

1. An X-ray energy distribution measurement apparatus comprising:
   a radiation detection device that has a plurality of radiation detectors each including a light emitting portion to which an X-ray is incident and arranged linearly in a line, and is insertable into a body of a patient;
   a dose rate measurement device that is connected to an optical fiber connected to the light emitting portion, receives a photon output from the light emitting portion, and obtains a dose rate at a position of the radiation detector on the basis of the photon;
   an irradiation direction determination device to which the dose rate is input from each dose rate measurement device separately connected to the light emitting portion of each of the radiation detectors, and determines whether or not a string of the radiation detectors including the plurality of radiation detectors arranged in a line, included in the radiation detection device, matches an X-ray irradiation direction on the basis of the input dose rate; and
   an energy distribution analysis device that obtains an X-ray energy distribution on the basis of the dose rate at each position of the plurality of radiation detectors included in the string of the radiation detectors matching the irradiation direction in a case where the irradiation direction determination device determines that the string of the radiation detectors matches the X-ray irradiation direction.

2. The X-ray energy distribution measurement apparatus according to claim 1,
wherein the light emitting portion contains at least one rare earth element.

3. The X-ray energy distribution measurement apparatus according to claim 1, further comprising:
a sensor insertion device that has a drive device rotating the radiation detection device; and
a drive control device that controls the drive device to rotate the radiation detection device in a case where the irradiation direction determination device determines that the string of the radiation detectors does not match the X-ray irradiation direction.

4. The X-ray energy distribution measurement apparatus according to claim 1,
wherein the radiation detection device includes a plurality of strings of radiation detectors including the plurality of radiation detectors arranged in a line,
wherein, among the plurality of radiation detectors included in the plurality of strings of radiation detectors, a single radiation detector located at a central axis of the radiation detectors is shared by the plurality of strings of radiation detectors, and
wherein the plurality of strings of radiation detectors are disposed with a gap therebetween around the central axis centering on the radiation detector located at the central axis.

5. The X-ray energy distribution measurement apparatus according to claim 1,
wherein the energy distribution analysis device obtains the X-ray energy distribution through inverse problem analysis by using the dose rate at each position of the plurality of radiation detectors included in the string of radiation detectors matching the irradiation direction.

6. The X-ray energy distribution measurement apparatus according to claim 1,
wherein the irradiation direction determination device determines whether or not a string of radiation detectors including the plurality of radiation detectors arranged in a line matches an X-ray irradiation direction by using the dose rate which is input from each dose rate measurement device, and reference dose rate information which is a determination reference regarding whether or not the dose rate from each dose rate measurement device matches the irradiation direction.

7. The X-ray energy distribution measurement apparatus according to claim 1,
wherein the dose rate measurement device includes
a conversion device that is connected to the optical fiber, and converts the photon output from the light emitting portion into an electric pulse,
a counting device that obtains a counting rate of the electric pulse output from the conversion device, and
a dose rate calculation unit that obtains the dose rate on the basis of the counting rate of the electric pulse.

8. The X-ray energy distribution measurement apparatus according to claim 6, further comprising:
a simulation device that obtains the reference dose rate information used to determine whether or not a string of radiation detectors including the plurality of radiation detectors arranged in a line matches an X-ray irradiation direction.

9. An X-ray therapy apparatus comprising:
an X-ray generation device that generates an X-ray;
a rotation gantry that is provided with the X-ray generation device;
a bed;
an irradiation head that is provided in the rotation gantry so as to face the bed; and
an X-ray energy distribution measurement apparatus,
wherein the X-ray energy distribution measurement apparatus has a radiation detection device that has a plurality of radiation detectors each including a light emitting portion to which an X-ray is incident and arranged linearly in a line, and is insertable into a body of a patient;
a dose rate measurement device that is connected to an optical fiber connected to the light emitting portion, receives a photon output from the light emitting portion, and obtains a dose rate at a position of the radiation detector on the basis of the photon; an irradiation direction determination device to which the dose rate is input from each dose rate measurement device separately connected to the light emitting portion of each of the radiation detectors, and determines whether or not a string of the radiation detectors including the plurality of radiation detectors arranged in a line, included in the radiation detection device, matches an X-ray irradiation direction on the basis of the input dose rate; and an energy distribution analysis device that obtains an X-ray energy distribution on the basis of the dose rate at each position of the plurality of radiation detectors included in the string of the radiation detectors matching the irradiation direction in a case where the irradiation direction determination device determines that the string of the radiation detectors matches the X-ray irradiation direction.

10. The X-ray therapy apparatus according to claim 9, further comprising:
a control device that outputs a stop control command to the X-ray generation device in a case where a dose obtained on the basis of information regarding the energy distribution obtained by the energy distribution analysis device is equal to or larger than a set dose.

* * * * *